(12) United States Patent
Bui

(10) Patent No.: US 8,545,435 B2
(45) Date of Patent: Oct. 1, 2013

(54) METHOD AND APPARATUS FOR PROVIDING MEDICAL TREATMENT THERAPY BASED ON CALCULATED DEMAND

(75) Inventor: Tuan Bui, Green Oaks, IL (US)

(73) Assignee: Baxter International, Inc., Deerfield, IL (US)

( * ) Notice: Subject to any disclaimer, the term of this patent is extended or adjusted under 35 U.S.C. 154(b) by 1083 days.

(21) Appl. No.: 11/078,805

(22) Filed: Mar. 11, 2005

(65) Prior Publication Data

US 2005/0182355 A1 Aug. 18, 2005

Related U.S. Application Data

(62) Division of application No. 10/038,516, filed on Jan. 3, 2002, now abandoned.

(51) Int. Cl.
*A61M 31/00* (2006.01)

(52) U.S. Cl.
USPC ............................................... 604/66; 604/67

(58) Field of Classification Search
USPC .................. 604/66, 67, 890.1, 891.1; 702/19
See application file for complete search history.

(56) References Cited

U.S. PATENT DOCUMENTS

| | | | |
|---|---|---|---|
| 2,705,223 A | 3/1955 | Renfrew et al. | |
| 2,971,876 A | 2/1961 | Phair | |
| 3,255,923 A | 6/1966 | Soto | |
| 3,375,300 A | 3/1968 | Ropp | |
| 3,428,828 A | 2/1969 | Korzekwa et al. | |
| 3,494,897 A | 2/1970 | Reding et al. | |
| 3,507,708 A | 4/1970 | Vingnaud | |
| 3,514,359 A | 5/1970 | Frese | |
| 3,561,493 A | 2/1971 | Maillard | |
| 3,645,992 A | 2/1972 | Elston | |
| 3,739,943 A | 6/1973 | Wilhelmson et al. | |

(Continued)

FOREIGN PATENT DOCUMENTS

| | | |
|---|---|---|
| DE | 1964735 | 7/1971 |
| DE | 133 411 Z | 1/1979 |

(Continued)

OTHER PUBLICATIONS

Opening Expert Witness Report of Dr. Juan Santiago Regarding Anticipation and Obviousness of the Claims of U.S. Patents Nos. 6,503,062 and 6,808,369 in view of the Prior Art and based on the Indefiniteness, Lack of Enablement, and Lack of Written Description of Certain Claims of U.S. Patent Nos. 6,503,062 and 6,808,369, Apr. 24, 2009.

(Continued)

*Primary Examiner* — Kevin C Sirmons
*Assistant Examiner* — Michael J Anderson
(74) *Attorney, Agent, or Firm* — K&L Gates LLP

(57) ABSTRACT

A medical treatment administration system for delivering a medical treatment to a patient. The system has a medical device, an electronic processor coupled to the medical device, and a sensor coupled to the processor. The sensor receives one or more signals which it transfers to the processor. The signals can be derived from the patient's physiological condition and/or the environment of the patient. The processor receives the signals and performs a calculation of the signal. Based on the result of the calculation, the processor regulates the distribution of medical treatment to the patient over a period of time.

20 Claims, 9 Drawing Sheets

(56) References Cited

U.S. PATENT DOCUMENTS

| | | |
|---|---|---|
| 3,772,136 A | 11/1973 | Workman |
| 3,814,799 A | 6/1974 | Wygasch |
| 3,816,033 A | 6/1974 | Fried et al. |
| 3,858,574 A | 1/1975 | Page |
| 3,858,581 A | 1/1975 | Kamen |
| 3,910,257 A | 10/1975 | Fletcher et al. |
| 3,912,843 A | 10/1975 | Brazier |
| 3,937,758 A | 2/1976 | Castagna |
| 3,995,084 A | 11/1976 | Berger et al. |
| 4,041,103 A | 8/1977 | Davison et al. |
| 4,058,647 A | 11/1977 | Inoue et al. |
| 4,071,040 A | 1/1978 | Moriarty |
| 4,087,587 A | 5/1978 | Shida et al. |
| 4,087,588 A | 5/1978 | Shida et al. |
| 4,095,012 A | 6/1978 | Schirmer |
| 4,110,303 A | 8/1978 | Gergen et al. |
| 4,122,947 A | 10/1978 | Falla |
| 4,137,915 A | 2/1979 | Kamen |
| 4,140,118 A | 2/1979 | Jassawalla |
| 4,142,524 A | 3/1979 | Jassawalla et al. |
| 4,147,827 A | 4/1979 | Breidt, Jr. et al. |
| 4,173,971 A | 11/1979 | Karz |
| 4,181,245 A | 1/1980 | Garrett et al. |
| 4,187,057 A | 2/1980 | Xanthopoulos |
| 4,211,519 A | 7/1980 | Hogan |
| 4,221,591 A | 9/1980 | Hogan |
| 4,233,367 A | 11/1980 | Ticknor et al. |
| 4,236,880 A | 12/1980 | Archibald |
| 4,243,619 A | 1/1981 | Fraser et al. |
| 4,265,601 A | 5/1981 | Mandroian |
| 4,286,597 A | 9/1981 | Gajewski |
| 4,298,714 A | 11/1981 | Levin et al. |
| 4,303,376 A | 12/1981 | Siekmann |
| 4,322,465 A | 3/1982 | Webster |
| 4,322,480 A | 3/1982 | Tuller et al. |
| D264,134 S | 4/1982 | Xanthopoulos |
| 4,327,726 A | 5/1982 | Kwong et al. |
| 4,332,655 A | 6/1982 | Berejka |
| 4,333,088 A | 6/1982 | Diggins |
| 4,336,352 A | 6/1982 | Sakurai et al. |
| 4,381,005 A | 4/1983 | Bujan |
| 4,382,753 A | 5/1983 | Archibald |
| 4,387,184 A | 6/1983 | Coquard et al. |
| 4,391,600 A | 7/1983 | Archibald |
| 4,405,667 A | 9/1983 | Christensen et al. |
| 4,405,774 A | 9/1983 | Miwa et al. |
| 4,407,877 A | 10/1983 | Rasmussen |
| 4,407,888 A | 10/1983 | Crofts |
| 4,410,164 A | 10/1983 | Kamen |
| 4,410,322 A | 10/1983 | Archibald |
| 4,411,649 A | 10/1983 | Kamen |
| 4,413,314 A | 11/1983 | Slater et al. |
| 4,417,753 A | 11/1983 | Bacehowski |
| 4,429,076 A | 1/1984 | Saito et al. |
| 4,438,238 A | 3/1984 | Fukushima et al. |
| 4,449,538 A | 5/1984 | Corbitt et al. |
| 4,449,976 A | 5/1984 | Kamen |
| 4,472,116 A | 9/1984 | Wenstrup |
| 4,472,117 A | 9/1984 | Wenstrup |
| 4,473,342 A | 9/1984 | Iles |
| 4,479,760 A | 10/1984 | Bilstad et al. |
| 4,479,761 A | 10/1984 | Bilstad et al. |
| 4,479,762 A | 10/1984 | Bilstad et al. |
| 4,479,989 A | 10/1984 | Mahal |
| 4,521,437 A | 6/1985 | Storms |
| 4,531,527 A | 7/1985 | Reinhold, Jr. et al. |
| 4,537,561 A | 8/1985 | Xanthopoulos |
| 4,547,136 A | 10/1985 | Rothstein |
| 4,548,348 A | 10/1985 | Clements |
| 4,561,443 A | 12/1985 | Hogrefe et al. |
| 4,562,118 A | 12/1985 | Maruhashi et al. |
| 4,568,723 A | 2/1986 | Lu |
| 4,573,994 A | 3/1986 | Fischell et al. |
| 4,574,173 A | 3/1986 | Bennett |
| 4,586,260 A | 5/1986 | Baxter et al. |
| 4,586,920 A | 5/1986 | Peabody |
| 4,588,648 A | 5/1986 | Krueger |
| 4,599,055 A | 7/1986 | Dykstra |
| 4,599,276 A | 7/1986 | Martini |
| 4,600,401 A | 7/1986 | Kamen |
| 4,602,642 A * | 7/1986 | O'Hara et al. ................ 600/474 |
| 4,620,690 A | 11/1986 | Kamen |
| 4,624,661 A | 11/1986 | Arimond |
| 4,627,844 A | 12/1986 | Schmitt |
| 4,628,969 A | 12/1986 | Jurgens, Jr. et al. |
| 4,634,426 A | 1/1987 | Kamen |
| 4,636,412 A | 1/1987 | Field |
| 4,640,870 A | 2/1987 | Akazawa et al. |
| 4,642,098 A | 2/1987 | Lundquist |
| 4,643,926 A | 2/1987 | Mueller |
| 4,648,872 A | 3/1987 | Kamen |
| 4,657,490 A | 4/1987 | Abbott |
| 4,668,752 A | 5/1987 | Tominari et al. |
| 4,673,334 A | 6/1987 | Allington et al. |
| 4,676,776 A | 6/1987 | Howson |
| 4,681,797 A | 7/1987 | Van Iseghem |
| 4,686,125 A | 8/1987 | Johnston et al. |
| 4,692,361 A | 9/1987 | Johnston et al. |
| 4,696,671 A | 9/1987 | Epstein et al. |
| 4,707,389 A | 11/1987 | Ward |
| 4,724,028 A | 2/1988 | Zabielski et al. |
| 4,726,997 A | 2/1988 | Mueller et al. |
| 4,731,051 A | 3/1988 | Fischell |
| 4,732,795 A | 3/1988 | Ohya et al. |
| 4,734,327 A | 3/1988 | Vicik |
| 4,735,558 A | 4/1988 | Kienholz et al. |
| 4,735,855 A | 4/1988 | Wofford et al. |
| 4,740,582 A | 4/1988 | Coquard et al. |
| 4,749,109 A | 6/1988 | Kamen |
| 4,753,222 A | 6/1988 | Morishita |
| 4,756,706 A | 7/1988 | Kerns et al. |
| 4,760,114 A | 7/1988 | Haaf et al. |
| 4,762,864 A | 8/1988 | Goel et al. |
| 4,764,404 A | 8/1988 | Genske et al. |
| 4,767,377 A | 8/1988 | Falla |
| 4,767,651 A | 8/1988 | Starczweski et al. |
| 4,772,497 A | 9/1988 | Maasola |
| 4,778,450 A | 10/1988 | Kamen |
| 4,778,451 A | 10/1988 | Kamen |
| 4,778,697 A | 10/1988 | Genske et al. |
| 4,786,697 A | 11/1988 | Cozewith et al. |
| 4,789,714 A | 12/1988 | Cozewith et al. |
| 4,792,488 A | 12/1988 | Schirmer |
| 4,794,942 A | 1/1989 | Yasuda et al. |
| 4,795,782 A | 1/1989 | Lutz et al. |
| 4,797,840 A | 1/1989 | Fraden |
| 4,798,580 A | 1/1989 | DeMeo et al. |
| 4,800,129 A | 1/1989 | Deak |
| 4,803,102 A | 2/1989 | Raniere et al. |
| 4,803,625 A | 2/1989 | Fu et al. |
| 4,808,161 A | 2/1989 | Kamen |
| 4,810,243 A | 3/1989 | Howson |
| 4,816,343 A | 3/1989 | Mueller |
| 4,818,190 A | 4/1989 | Pelmulder et al. |
| 4,824,339 A | 4/1989 | Bainbridge et al. |
| 4,826,482 A | 5/1989 | Kamen |
| 4,828,545 A | 5/1989 | Epstein et al. |
| 4,834,755 A | 5/1989 | Silvestrini et al. |
| 4,842,948 A | 6/1989 | Gagliani et al. |
| 4,848,722 A | 7/1989 | Webster |
| 4,850,972 A | 7/1989 | Schulman et al. |
| 4,852,851 A | 8/1989 | Webster |
| 4,855,356 A | 8/1989 | Holub et al. |
| 4,856,259 A | 8/1989 | Woo et al. |
| 4,856,260 A | 8/1989 | Woo et al. |
| 4,861,242 A | 8/1989 | Finsterwald |
| 4,863,996 A | 9/1989 | Nakazima et al. |
| 4,865,584 A | 9/1989 | Epstein et al. |
| 4,871,351 A | 10/1989 | Feingold |
| 4,871,799 A | 10/1989 | Kobayashi et al. |
| 4,872,813 A | 10/1989 | Gorton et al. |
| 4,873,287 A | 10/1989 | Holub et al. |
| 4,877,682 A | 10/1989 | Sauers et al. |
| 4,885,119 A | 12/1989 | Mueller et al. |

| | | | | | | |
|---|---|---|---|---|---|---|
| 4,886,431 A | 12/1989 | Soderquist et al. | | 5,178,182 A | 1/1993 | Kamen |
| 4,901,221 A | 2/1990 | Kodosky et al. | | 5,183,706 A | 2/1993 | Bekele |
| 4,904,168 A | 2/1990 | Cavoto et al. | | 5,185,084 A | 2/1993 | Lapidus et al. |
| 4,910,085 A | 3/1990 | Raniere et al. | | 5,185,189 A | 2/1993 | Stenger et al. |
| 4,922,930 A * | 5/1990 | Adkins et al. ............ 607/19 | | 5,189,091 A | 2/1993 | Laughner |
| 4,923,470 A | 5/1990 | Dumican | | 5,191,891 A | 3/1993 | Righter |
| 4,925,444 A | 5/1990 | Orkin et al. | | 5,193,913 A | 3/1993 | Rosenbaum |
| 4,929,479 A | 5/1990 | Shishido et al. | | 5,193,990 A | 3/1993 | Kamen et al. |
| 4,931,520 A | 6/1990 | Yamanashi et al. | | 5,194,316 A | 3/1993 | Horner et al. |
| 4,933,843 A | 6/1990 | Scheller et al. | | 5,195,960 A | 3/1993 | Hossain et al. |
| 4,937,299 A | 6/1990 | Ewen et al. | | 5,195,986 A | 3/1993 | Kamen |
| 4,941,519 A | 7/1990 | Sestak et al. | | 5,196,254 A | 3/1993 | Akiyama |
| 4,942,514 A | 7/1990 | Miyagaki et al. | | 5,203,943 A | 4/1993 | Nornberg et al. |
| 4,946,616 A | 8/1990 | Falla et al. | | 5,206,290 A | 4/1993 | Mizuno et al. |
| 4,950,720 A | 8/1990 | Randall, Jr. et al. | | 5,207,642 A | 5/1993 | Orkin et al. |
| 4,952,928 A | 8/1990 | Carroll et al. | | 5,207,983 A | 5/1993 | Liebert et al. |
| 4,957,966 A | 9/1990 | Nishio et al. | | 5,211,201 A | 5/1993 | Kamen et al. |
| 4,957,967 A | 9/1990 | Mizuno et al. | | 5,212,238 A | 5/1993 | Scheibelhoffer et al. |
| 4,966,795 A | 10/1990 | Genske et al. | | 5,213,099 A | 5/1993 | Tripp, Jr. |
| 4,976,162 A | 12/1990 | Kamen | | 5,213,483 A | 5/1993 | Flaherty et al. |
| 4,977,213 A | 12/1990 | Giroud-Abel et al. | | 5,215,312 A | 6/1993 | Knappe et al. |
| 4,990,054 A | 2/1991 | Janocko | | 5,218,048 A | 6/1993 | Abe et al. |
| 4,992,511 A | 2/1991 | Yamamoto et al. | | 5,218,049 A | 6/1993 | Yamamoto et al. |
| 4,995,268 A | 2/1991 | Ash et al. | | 5,222,946 A | 6/1993 | Kamen |
| 4,996,054 A | 2/1991 | Pietsch et al. | | 5,226,425 A | 7/1993 | Righter |
| 4,999,254 A | 3/1991 | Ofstein | | 5,230,623 A | 7/1993 | Guthrie et al. |
| 5,003,019 A | 3/1991 | Ishimaru et al. | | 5,230,934 A | 7/1993 | Sakano et al. |
| 5,006,601 A | 4/1991 | Lutz et al. | | 5,230,935 A | 7/1993 | Delimoy et al. |
| 5,008,204 A | 4/1991 | Stehling | | 5,238,997 A | 8/1993 | Bauer et al. |
| 5,008,356 A | 4/1991 | Ishimaru et al. | | 5,241,985 A | 9/1993 | Faust et al. |
| 5,017,652 A | 5/1991 | Abe et al. | | 5,244,971 A | 9/1993 | Dekonick |
| 5,019,140 A | 5/1991 | Bowser et al. | | 5,245,151 A | 9/1993 | Chamberlain et al. |
| 5,034,457 A | 7/1991 | Serini et al. | | 5,252,044 A | 10/1993 | Raines et al. |
| 5,034,458 A | 7/1991 | Serini et al. | | 5,254,824 A | 10/1993 | Chamberlain et al. |
| 5,038,800 A | 8/1991 | Oba | | 5,256,157 A | 10/1993 | Samiotes et al. |
| 5,043,088 A | 8/1991 | Falla | | 5,257,917 A | 11/1993 | Minarik et al. |
| 5,044,902 A | 9/1991 | Malbec | | 5,258,230 A | 11/1993 | La Fleur et al. |
| 5,053,457 A | 10/1991 | Lee | | 5,272,235 A | 12/1993 | Wakatsuru et al. |
| 5,062,774 A | 11/1991 | Kramer et al. | | 5,278,231 A | 1/1994 | Chundury |
| 5,071,686 A | 12/1991 | Genske et al. | | 5,278,377 A | 1/1994 | Tsai |
| 5,071,911 A | 12/1991 | Furuta et al. | | 5,288,531 A | 2/1994 | Falla et al. |
| 5,071,912 A | 12/1991 | Furuta et al. | | 5,288,560 A | 2/1994 | Sudo et al. |
| 5,075,376 A | 12/1991 | Furuta et al. | | 5,288,799 A | 2/1994 | Schmid et al. |
| 5,078,683 A | 1/1992 | Sancoff et al. | | 5,290,856 A | 3/1994 | Okamoto |
| 5,079,295 A | 1/1992 | Furuta et al. | | 5,291,190 A | 3/1994 | Scarola et al. |
| 5,085,649 A | 2/1992 | Flynn | | 5,294,763 A | 3/1994 | Chamberlain et al. |
| 5,087,677 A | 2/1992 | Brekner et al. | | 5,295,062 A | 3/1994 | Fukushima |
| 5,088,515 A | 2/1992 | Kamen | | 5,297,554 A | 3/1994 | Glynn et al. |
| 5,093,164 A | 3/1992 | Bauer et al. | | 5,302,093 A | 4/1994 | Owens et al. |
| 5,093,194 A | 3/1992 | Touhsaent et al. | | 5,306,542 A | 4/1994 | Bayer |
| 5,094,820 A | 3/1992 | Maxwell et al. | | 5,312,867 A | 5/1994 | Mitsuno et al. |
| 5,094,921 A | 3/1992 | Itamura et al. | | 5,317,059 A | 5/1994 | Chundury et al. |
| 5,098,262 A | 3/1992 | Wecker et al. | | 5,317,506 A | 5/1994 | Coutré et al. |
| 5,100,380 A | 3/1992 | Epstein et al. | | 5,331,057 A | 7/1994 | Brekner et al. |
| 5,106,366 A | 4/1992 | Steppe | | 5,336,190 A | 8/1994 | Moss et al. |
| 5,108,844 A | 4/1992 | Blemberg et al. | | 5,338,157 A | 8/1994 | Blomquist |
| 5,109,849 A | 5/1992 | Goodman et al. | | 5,342,886 A | 8/1994 | Glotin et al. |
| 5,110,642 A | 5/1992 | Genske et al. | | 5,348,794 A | 9/1994 | Takahashi |
| 5,115,133 A | 5/1992 | Knudson | | 5,350,357 A | 9/1994 | Kamen et al. |
| 5,116,312 A | 5/1992 | Blankenship et al. | | 5,356,676 A | 10/1994 | Von Widdern et al. |
| 5,116,906 A | 5/1992 | Mizuno et al. | | 5,359,001 A | 10/1994 | Epple et al. |
| 5,125,891 A | 6/1992 | Hossain et al. | | 5,360,648 A | 11/1994 | Falla et al. |
| 5,129,894 A | 7/1992 | Sommermeyer et al. | | 5,361,758 A | 11/1994 | Hall et al. |
| 5,132,363 A | 7/1992 | Furuta et al. | | 5,364,371 A | 11/1994 | Kamen |
| 5,133,650 A | 7/1992 | Sunderland et al. | | 5,364,486 A | 11/1994 | Falla et al. |
| 5,135,485 A | 8/1992 | Cohen et al. | | 5,368,562 A | 11/1994 | Blomquist et al. |
| 5,135,785 A | 8/1992 | Milton | | 5,371,151 A | 12/1994 | Berge et al. |
| 5,137,023 A | 8/1992 | Mendelson et al. | | 5,376,070 A | 12/1994 | Purvis et al. |
| 5,145,731 A | 9/1992 | Lund et al. | | 5,378,231 A | 1/1995 | Johnson et al. |
| 5,152,296 A | 10/1992 | Simons | | 5,378,543 A | 1/1995 | Murata et al. |
| 5,153,827 A | 10/1992 | Coutré et al. | | 5,378,800 A | 1/1995 | Mok et al. |
| 5,154,979 A | 10/1992 | Kerschbaumer et al. | | 5,382,630 A | 1/1995 | Stehling et al. |
| 5,155,693 A | 10/1992 | Altmayer et al. | | 5,382,631 A | 1/1995 | Stehling et al. |
| 5,159,004 A | 10/1992 | Furuta et al. | | 5,385,540 A | 1/1995 | Abbott et al. |
| 5,164,267 A | 11/1992 | D'Heur et al. | | 5,387,645 A | 2/1995 | Montag et al. |
| 5,165,874 A | 11/1992 | Sancoff et al. | | 5,395,321 A | 3/1995 | Kawahara et al. |
| 5,167,235 A | 12/1992 | Seacord et al. | | 5,395,329 A | 3/1995 | Fleischhacker et al. |
| 5,176,634 A | 1/1993 | Smith et al. | | 5,397,222 A | 3/1995 | Moss et al. |
| 5,176,956 A | 1/1993 | Jevne et al. | | 5,400,246 A | 3/1995 | Wilson et al. |

| Patent | Date | Inventor(s) |
|---|---|---|
| 5,401,342 A | 3/1995 | Vincent et al. |
| 5,409,355 A | 4/1995 | Brooke |
| 5,412,400 A | 5/1995 | Takahara et al. |
| 5,421,823 A | 6/1995 | Kamen et al. |
| 5,422,409 A | 6/1995 | Brekner et al. |
| 5,427,509 A | 6/1995 | Chapman et al. |
| 5,429,485 A | 7/1995 | Dodge |
| 5,429,602 A | 7/1995 | Hauser |
| 5,431,626 A | 7/1995 | Bryant et al. |
| 5,433,588 A | 7/1995 | Monk et al. |
| 5,438,510 A | 8/1995 | Bryant et al. |
| 5,439,587 A | 8/1995 | Stankowski et al. |
| 5,442,919 A | 8/1995 | Wilhelm |
| 5,445,506 A | 8/1995 | Afflerbaugh et al. |
| 5,446,270 A | 8/1995 | Chamberlain et al. |
| 5,457,249 A | 10/1995 | Sagane et al. |
| 5,460,490 A | 10/1995 | Carr et al. |
| 5,460,493 A | 10/1995 | Deniega et al. |
| 5,462,416 A | 10/1995 | Dennehy et al. |
| 5,464,388 A | 11/1995 | Merte et al. |
| 5,469,855 A | 11/1995 | Pompei et al. |
| 5,474,552 A | 12/1995 | Palti |
| 5,474,683 A | 12/1995 | Bryant et al. |
| 5,475,060 A | 12/1995 | Brekner et al. |
| 5,480,294 A | 1/1996 | Di Perna et al. |
| 5,482,440 A | 1/1996 | Dennehey et al. |
| 5,482,446 A | 1/1996 | Williamson et al. |
| 5,482,770 A | 1/1996 | Bekele |
| 5,485,408 A | 1/1996 | Blomquist |
| 5,487,649 A | 1/1996 | Dorsey, III et al. |
| 5,498,677 A | 3/1996 | Weller |
| 5,508,051 A | 4/1996 | Falla et al. |
| 5,509,422 A | 4/1996 | Fukami |
| 5,518,378 A | 5/1996 | Neftel et al. |
| 5,522,396 A | 6/1996 | Langer et al. |
| 5,522,769 A | 6/1996 | DeGuiseppi |
| 5,525,659 A | 6/1996 | Falla et al. |
| 5,526,844 A | 6/1996 | Kamen |
| 5,529,708 A | 6/1996 | Palmgren et al. |
| 5,530,065 A | 6/1996 | Farley et al. |
| 5,533,589 A | 7/1996 | Critzer |
| 5,534,606 A | 7/1996 | Bennett et al. |
| 5,540,808 A | 7/1996 | Vincent et al. |
| 5,542,919 A | 8/1996 | Simon et al. |
| 5,544,651 A | 8/1996 | Wilk |
| 5,552,504 A | 9/1996 | Bennett et al. |
| 5,554,013 A | 9/1996 | Owens et al. |
| 5,558,638 A | 9/1996 | Evers et al. |
| 5,558,640 A | 9/1996 | Pfeiler et al. |
| 5,569,026 A | 10/1996 | Novak |
| 5,569,187 A | 10/1996 | Kaiser |
| 5,570,716 A | 11/1996 | Kamen et al. |
| 5,573,506 A | 11/1996 | Vasko |
| 5,575,310 A | 11/1996 | Kamen et al. |
| 5,575,632 A | 11/1996 | Morris et al. |
| 5,578,012 A | 11/1996 | Kamen et al. |
| 5,580,914 A | 12/1996 | Falla et al. |
| 5,582,593 A | 12/1996 | Hultman |
| 5,583,192 A | 12/1996 | Bennett et al. |
| 5,586,868 A | 12/1996 | Lawless et al. |
| 5,588,815 A | 12/1996 | Zaleski, II |
| 5,588,816 A | 12/1996 | Abbott et al. |
| 5,601,420 A | 2/1997 | Warner et al. |
| 5,609,572 A | 3/1997 | Lang |
| 5,609,575 A | 3/1997 | Larson et al. |
| 5,610,253 A | 3/1997 | Hatke et al. |
| 5,620,312 A | 4/1997 | Hyman et al. |
| 5,620,425 A | 4/1997 | Heffernan et al. |
| 5,628,908 A | 5/1997 | Kamen et al. |
| 5,629,398 A | 5/1997 | Okamoto et al. |
| 5,634,896 A | 6/1997 | Bryant et al. |
| 5,637,100 A | 6/1997 | Sudo |
| 5,637,400 A | 6/1997 | Brekner et al. |
| 5,643,212 A | 7/1997 | Coutrë et al. |
| 5,650,471 A | 7/1997 | Abe et al. |
| 5,653,739 A * | 8/1997 | Maurer et al. ............. 604/890.1 |
| 5,655,897 A | 8/1997 | Neftel et al. |
| 5,658,250 A | 8/1997 | Blomquist et al. |
| 5,674,944 A | 10/1997 | Falla et al. |
| 5,676,530 A | 10/1997 | Nazarifar |
| 5,686,527 A | 11/1997 | Laurin et al. |
| 5,693,728 A | 12/1997 | Okamoto et al. |
| 5,697,899 A * | 12/1997 | Hillman et al. ................. 604/28 |
| 5,698,645 A | 12/1997 | Weller et al. |
| 5,698,654 A | 12/1997 | Nye et al. |
| 5,707,751 A | 1/1998 | Garza et al. |
| 5,711,654 A | 1/1998 | Afflerbaugh |
| 5,718,569 A | 2/1998 | Holst |
| 5,721,025 A | 2/1998 | Falla et al. |
| 5,723,189 A | 3/1998 | Sudo |
| 5,730,720 A * | 3/1998 | Sites et al. ...................... 604/27 |
| 5,733,991 A | 3/1998 | Rohrmann et al. |
| 5,741,125 A | 4/1998 | Neftel et al. |
| 5,744,664 A | 4/1998 | Brekner et al. |
| 5,752,813 A | 5/1998 | Tyner et al. |
| 5,756,623 A | 5/1998 | Kreuder et al. |
| 5,760,760 A | 6/1998 | Helms |
| 5,782,575 A | 7/1998 | Vincent et al. |
| 5,788,670 A | 8/1998 | Reinhard et al. |
| 5,788,671 A | 8/1998 | Johnson |
| 5,792,824 A | 8/1998 | Natori |
| 5,795,945 A | 8/1998 | Natori |
| 5,807,336 A | 9/1998 | Russo et al. |
| 5,816,779 A | 10/1998 | Lawless et al. |
| 5,849,843 A | 12/1998 | Laurin et al. |
| 5,854,347 A | 12/1998 | Laurin et al. |
| 5,854,349 A | 12/1998 | Abe et al. |
| 5,863,986 A | 1/1999 | Herrmann-Schonherr et al. |
| 5,871,566 A | 2/1999 | Rutz |
| 5,872,201 A | 2/1999 | Cheung et al. |
| 5,875,109 A * | 2/1999 | Federspiel ..................... 700/40 |
| 5,879,768 A | 3/1999 | Falla et al. |
| 5,885,245 A | 3/1999 | Lynch et al. |
| 5,895,371 A | 4/1999 | Levitas et al. |
| 5,899,674 A | 5/1999 | Jung et al. |
| 5,901,246 A * | 5/1999 | Hoffberg et al. .............. 382/209 |
| 5,906,598 A | 5/1999 | Giesler et al. |
| 5,919,209 A * | 7/1999 | Schouten ........................... 607/2 |
| 5,920,477 A * | 7/1999 | Hoffberg et al. .............. 382/181 |
| 5,927,956 A | 7/1999 | Lim et al. |
| 5,928,196 A | 7/1999 | Johnson et al. |
| 5,931,808 A | 8/1999 | Pike |
| 5,935,099 A | 8/1999 | Peterson et al. |
| 5,942,579 A | 8/1999 | Falla et al. |
| 5,978,702 A | 11/1999 | Ward et al. |
| 5,980,495 A | 11/1999 | Heinz et al. |
| 5,983,136 A | 11/1999 | Kamen |
| 5,984,762 A | 11/1999 | Tedeschi et al. |
| 5,989,423 A | 11/1999 | Kamen et al. |
| 5,990,254 A | 11/1999 | Weller et al. |
| 5,993,949 A | 11/1999 | Rosenbaum et al. |
| 5,998,019 A | 12/1999 | Rosenbaum et al. |
| 6,001,201 A | 12/1999 | Vincent et al. |
| 6,007,520 A | 12/1999 | Sudo |
| 6,017,318 A * | 1/2000 | Gauthier et al. ............... 600/578 |
| 6,020,444 A | 2/2000 | Riedel et al. |
| 6,036,458 A | 3/2000 | Cole et al. |
| 6,045,648 A | 4/2000 | Palmgren et al. |
| 6,053,887 A | 4/2000 | Levita et al. |
| 6,056,522 A | 5/2000 | Johnson |
| 6,059,544 A | 5/2000 | Jung et al. |
| 6,060,572 A | 5/2000 | Gillis et al. |
| 6,065,270 A | 5/2000 | Reinhard et al. |
| 6,068,936 A | 5/2000 | Peiffer et al. |
| 6,070,761 A | 6/2000 | Bloom et al. |
| 6,074,183 A | 6/2000 | Allen et al. |
| 6,077,246 A | 6/2000 | Kullas et al. |
| 6,096,061 A * | 8/2000 | Alt et al. ............................ 607/4 |
| 6,106,948 A | 8/2000 | Wang et al. |
| 6,109,269 A | 8/2000 | Rise et al. |
| 6,109,895 A | 8/2000 | Ray et al. |
| 6,110,549 A | 8/2000 | Hamada et al. |
| 6,110,617 A | 8/2000 | Feres |
| 6,114,457 A | 9/2000 | Markel et al. |
| 6,117,465 A | 9/2000 | Falla et al. |
| 6,121,394 A | 9/2000 | Sugimoto et al. |
| 6,129,699 A | 10/2000 | Haight et al. |
| 6,136,744 A | 10/2000 | Gillis et al. |

| | | |
|---|---|---|
| 6,147,025 A | 11/2000 | Gillis et al. |
| 6,165,154 A | 12/2000 | Gray et al. |
| 6,168,862 B1 | 1/2001 | Rosenbaum et al. |
| 6,169,052 B1 | 1/2001 | Brekner et al. |
| 6,169,981 B1 * | 1/2001 | Werbos .......................... 706/23 |
| 6,171,670 B1 | 1/2001 | Sudo et al. |
| 6,186,752 B1 | 2/2001 | Deniega et al. |
| 6,191,254 B1 | 2/2001 | Falla et al. |
| 6,203,296 B1 | 3/2001 | Ray et al. |
| 6,210,361 B1 | 4/2001 | Kamen et al. |
| 6,221,648 B1 | 4/2001 | La Page et al. |
| 6,225,426 B1 | 5/2001 | Gillis et al. |
| 6,225,427 B1 | 5/2001 | Burton et al. |
| 6,231,320 B1 | 5/2001 | Lawless et al. |
| 6,234,006 B1 * | 5/2001 | Sunshine et al. ............. 73/29.01 |
| 6,234,997 B1 | 5/2001 | Kamen et al. |
| RE37,208 E | 6/2001 | Winter et al. |
| 6,248,093 B1 | 6/2001 | Moberg |
| 6,249,700 B1 * | 6/2001 | Alt ................................... 607/4 |
| 6,255,396 B1 | 7/2001 | Ding et al. |
| 6,261,655 B1 | 7/2001 | Rosenbaum et al. |
| 6,266,664 B1 | 7/2001 | Russell-Falla et al. |
| 6,280,408 B1 | 8/2001 | Sipin |
| 6,280,409 B1 * | 8/2001 | Stone et al. ...................... 604/67 |
| 6,293,926 B1 | 9/2001 | Sorensen et al. |
| 6,302,653 B1 | 10/2001 | Bryant et al. |
| 6,317,700 B1 * | 11/2001 | Bagne ........................ 604/890.1 |
| 6,343,614 B1 | 2/2002 | Gray et al. |
| 6,364,857 B1 | 4/2002 | Gray et al. |
| 6,372,848 B1 | 4/2002 | Yang et al. |
| 6,382,923 B1 | 5/2002 | Gray |
| 6,398,727 B1 * | 6/2002 | Bui et al. ....................... 600/300 |
| 6,416,293 B1 | 7/2002 | Bouchard |
| 6,454,707 B1 * | 9/2002 | Casscells et al. ............. 600/300 |
| 6,468,242 B1 | 10/2002 | Wilson et al. |
| 6,497,676 B1 | 12/2002 | Childers et al. |
| 6,503,062 B1 | 1/2003 | Gray et al. |
| 6,562,001 B2 * | 5/2003 | Lebel et al. ...................... 604/65 |
| 6,562,002 B1 | 5/2003 | Taylor |
| 6,579,242 B2 * | 6/2003 | Bui et al. ....................... 600/537 |
| 6,592,542 B2 | 7/2003 | Childers et al. |
| 6,689,091 B2 * | 2/2004 | Bui et al. ......................... 604/67 |
| 6,737,629 B2 | 5/2004 | Nixon et al. |
| 6,808,369 B2 | 10/2004 | Gray et al. |
| 6,814,547 B2 | 11/2004 | Childers et al. |
| 6,821,249 B2 * | 11/2004 | Casscells et al. ............. 600/300 |
| 6,830,549 B2 * | 12/2004 | Bui et al. ....................... 600/549 |
| 6,869,538 B2 | 3/2005 | Yu et al. |
| 7,033,539 B2 | 4/2006 | Krensky et al. |
| 7,117,019 B2 | 10/2006 | Abbasi |
| 7,268,775 B1 | 9/2007 | Gettemy |
| 7,410,475 B2 | 8/2008 | Krensky et al. |
| 8,250,483 B2 * | 8/2012 | Blomquist .................... 715/771 |
| 2001/0039824 A1 * | 11/2001 | Sunshine et al. ............. 73/29.01 |
| 2002/0019586 A1 * | 2/2002 | Teller et al. .................... 600/300 |
| 2002/0077598 A1 | 6/2002 | Yap et al. |
| 2002/0138017 A1 * | 9/2002 | Bui et al. ....................... 600/537 |
| 2002/0143290 A1 * | 10/2002 | Bui et al. ......................... 604/67 |
| 2003/0004652 A1 * | 1/2003 | Brunner et al. ................. 702/19 |
| 2003/0083822 A2 * | 5/2003 | Brunner et al. ................. 702/19 |
| 2003/0092975 A1 * | 5/2003 | Casscells et al. ............. 600/300 |
| 2003/0100998 A2 * | 5/2003 | Brunner et al. ................. 702/19 |
| 2003/0125662 A1 * | 7/2003 | Bui ................................. 604/67 |
| 2003/0130590 A1 * | 7/2003 | Bui et al. ....................... 600/537 |
| 2003/0140928 A1 * | 7/2003 | Bui et al. ....................... 128/898 |
| 2003/0195454 A1 | 10/2003 | Wariar et al. |
| 2003/0204162 A1 | 10/2003 | Childers et al. |
| 2003/0220609 A1 | 11/2003 | Childers et al. |
| 2004/0254513 A1 | 12/2004 | Shang et al. |
| 2005/0055242 A1 * | 3/2005 | Bello et al. ........................ 705/2 |
| 2005/0118038 A1 | 6/2005 | Gray et al. |
| 2005/0182355 A1 * | 8/2005 | Bui ................................. 604/66 |
| 2006/0007223 A1 | 1/2006 | Parker |
| 2006/0181552 A1 | 8/2006 | Hopple |
| 2008/0186707 A1 | 8/2008 | Ku et al. |
| 2008/0200865 A1 | 8/2008 | Bedingfield |
| 2008/0200866 A1 | 8/2008 | Prisco et al. |
| 2008/0200867 A1 | 8/2008 | Bedingfield |
| 2008/0200868 A1 | 8/2008 | Alberti et al. |
| 2008/0200869 A1 | 8/2008 | Bedingfield |

FOREIGN PATENT DOCUMENTS

| | | |
|---|---|---|
| DE | 251 904 A3 | 12/1987 |
| DE | 39 37 865 A1 | 6/1990 |
| EP | 0 028 371 | 5/1981 |
| EP | 0028371 | 5/1981 |
| EP | 0 156 464 A1 | 10/1985 |
| EP | 0 204 260 | 12/1986 |
| EP | 0204260 | 12/1986 |
| EP | 0 291 208 A2 | 11/1988 |
| EP | 0 306 664 A2 | 3/1989 |
| EP | 0 319 272 | 6/1989 |
| EP | 0319272 | 6/1989 |
| EP | 0 402 505 | 12/1990 |
| EP | 0402505 | 12/1990 |
| EP | 91/02484 | 3/1991 |
| EP | 0 011 935 | 5/1991 |
| EP | 0011935 | 8/1991 |
| EP | 0 216 509 B1 | 9/1991 |
| EP | 0 248 632 | 4/1992 |
| EP | 0248632 | 4/1992 |
| EP | 0 497 567 A2 | 8/1992 |
| EP | 0 524 802 A1 | 1/1993 |
| EP | 0 283 164 B1 | 5/1995 |
| EP | 0 492 982 B1 | 8/1995 |
| EP | 0 430 585 B1 | 1/1996 |
| EP | 0 156 464 B1 | 5/1996 |
| EP | 0 582 355 B1 | 5/1996 |
| EP | 0 709 105 A1 | 5/1996 |
| EP | 0 203 799 B1 | 8/1996 |
| EP | 0 384 694 B1 | 9/1996 |
| EP | 0 497 567 B1 | 9/1996 |
| EP | 0 291 208 B1 | 8/1997 |
| EP | 0 790 063 A1 | 8/1997 |
| EP | 0 680 401 B1 | 1/1999 |
| EP | 0 709 105 B1 | 12/2001 |
| FR | 2371931 | 6/1978 |
| FR | 2440740 | 6/1980 |
| GB | 1326236 | 8/1973 |
| GB | 2285329 | 7/1995 |
| JP | 03-095286 | 4/1991 |
| JP | 05-277154 | 10/1993 |
| JP | 11-071554 | 3/1999 |
| SE | 331736 | 1/1971 |
| TW | 360523 | 4/2008 |
| WO | 84/02473 | 7/1984 |
| WO | 85/04813 | 11/1985 |
| WO | 86/01115 | 2/1986 |
| WO | 91/02484 | 3/1991 |
| WO | 92/15349 | 9/1992 |
| WO | 93/01845 | 2/1993 |
| WO | 95/35124 | 12/1995 |
| WO | 97/08054 | 3/1997 |
| WO | 98/27926 | 7/1998 |
| WO | 98/44043 | 10/1998 |
| WO | 99/06082 | 2/1999 |
| WO | WO 9932174 | 7/1999 |
| WO | 99/48990 | 9/1999 |
| WO | WO 0154753 | 8/2001 |
| WO | 01/91829 | 12/2001 |

OTHER PUBLICATIONS

Opening Expert Witness Report of William K. Durfee Regarding whether Certain Claims of U.S. Patent No. 5,324,422, U.S. Patent No. 5,421,823, U.S. Patent No. 5,431,626 and U.S. Patent No. 5,438,510 were Ready for Patenting, Apr. 24, 2009.

Expert Witness Report of Fred K. Forster: Analysis of Obviousness of Certain Asserted Claims of U.S. Patent Nos. 5,431,626; 5,324,422; and 5,438,510, Apr. 24, 2009.

Expert Witness Report of Ronald J. Adrian Regarding Lack of Written Description, Lack of Enablement, and Indefiniteness of the Asserted Claim (Claim 12) of U.S. Patent No. 6,814,547, Apr. 24, 2009.

Exhibit A, Credentials of Ronald J. Adrian.

Exhibit B, Materials Considered by Ronald J. Adrian.
Expert Report on Development of the PD700 and Motivation to Combine the PD700 and U.S. Patent No. 5,088,515, Sven Olofsson, Apr. 24, 2009.
Expert Witness Report of Juan G. Santiago Regarding Lack of Written Description, Non-Enablement, and Indefiniteness of the Asserted Claims of U.S. Patent Nos. 5,421,823; 5,324,422; 5,438,510; and 5,431,626, Apr. 24, 2009.
Opening Expert Witness Report of Dr. Martin Roberts Regarding a History of Peritoneal Dialysis and the Obviousness and Consequent Invalidity of the Asserted Claims of U.S. Patent No. 5,421,823, Apr. 24, 2009.
Opening Expert Witness Report of Dr. Darrell Long Regarding Technical Features of the High Flow Peritoneal Dialysis and Personal Cycler Machines, Apr. 24, 2009.
Defendants' Preliminary Invalidity Contentions for U.S. Patent No. 6,929,751, Baxter Healthcare Corporation v. Fresenius Medical Care Holdings, Case No. C 07-01359 PJH (JL), filed Jan. 31, 2008.
Defendants' Preliminary Invalidity Contentions for U.S. Patent No. 7,083,719, Baxter Healthcare Corporation v. Fresenius Medical Care Holdings, Case No. C 07-01359 PJH (JL), filed Jan. 31, 2008.
Defendants' Final Invalidity Contentions for U.S. Patent No. 6,814,547, Baxter Healthcare Corporation v. Fresenius Medical Care Holdings, Case No. C 07-01359 PJH (JL), filed Apr. 1, 2009.
Fresenius 90/2 Peritoneal Therapy Cycler (on information and belief, on sale in United States by 1991).
Blumenkrantz et al., Applications of the Redy Sorbent System to Hemodialysis and Peritoneal Dialysis, Artificial Organs, vol. 3, No. 3 (Aug. 1979).
Blumenkrantz et al., Development of a Sorbent Peritoneal Dialysate Regeneration System—A Progress Report, European Dialysis and Transplant Association 1978.
Blumenkrantz and Roberts, Progress in Peritoneal Dialysis: a Historical Prospective, Contributions to Nephrology, vol. 17, pp. 101-110 (1979).
Diaz-Buxo, CCPD is even better than CAPD, Kidney International, vol. 28, Suppl. 17, pp. S-26-S-28 (1985).
Diaz-Buxo, CCPD Technique and Current Clinical Experience (1982).
Diaz-Buxo, et al., Continuous Cyclic Peritoneal Dialysis: A Preliminary Report, Artificial Organs, vol. 5, No. 2, pp. 157-161 (May 1981).
Diaz-Buxo, Current Status of Continuous Cyclic Peritoneal Dialysis (CCPD), Peritoneal Dialysis International, vol. 9, pp. 9-14 (1989).
Diaz-Buxo, Issues in Nephrology: Continuous Cyclic Peritoneal Dialysis, NAPHT News, Feb. 1983, pp. 12-14.
Diaz-Buxo, Peritoneal Dialysis Reverse Osmosis Machines and Cyclers, Dialysis Therapy, pp. 41-48 (1986).
Drukker et al., Replacement of Renal Function by Dialysis, 2nd Ed., Ch. 21, 1983.
Lewin and Maxwell, Sorbent-Based Regenerating Peritoneal Dialysis, Sorbents and Their Clinical Applications, pp. 353-374 (1980).
Lewin et al., Sorbent for Application in the Treatment of ESRD Patients, Annual Progress Report re Contract #N01-AM-9-2215, submitted Jun. 22, 1982.
Ratnu, et al., A New Technique—Semicontinuous Rapid Flow, High Volume Exchange—For Effective Peritoneal Dialysis in Shorter Periods, Nephron, vol. 31, pp. 159-163 (1982).
Twardowski, Peritoneal Dialysis: Current Technology and techniques, Postgraduate Medicine, vol. 85, No. 5 (Apr. 1989).
Product Evaluation Reports: Peritoneal Dialysis Machine "Pac-X," Hospital Materials Management, vol. 12, No. 11, p. 16 (Nov. 1987).
Brochure entitled, AP Hauni: Automatisches Peritonealdialyse-Great (1970).
Brochure entitled, Fresenius Delivers 90/2 Peritoneal Therapy Cycler.
Brochure entitled, REDY Universal Re-circulating Dialysate System.
Brochure entitled, SIF 901 Perugia.
Translation of brochure entitled, SIF 901 Perugia.
Translation of Certificate for translation of brochure entitled, SIF 901 Perugia.
Operators Instructions for Fresenius 90/2 Peritoneal Therapy Cycler.
Photo of dialysis patient connected to machine.
Photo of dialysis machine.
Peritoneal Dialyser PD700 Service Manual, Jun. 1977.
Peritoneal Dialyser PD700 Instruction Manual.
PD700 Peritoneal Dialyser Users Hand-book, Dec. 1977.
Operating Instructions, Peritoneal Dialyser PD700, for Ser. No. 300.
Brochure entitled, Peritoneal Dialyser PD700, May 1979.
Brochure entitled, for Volume Measurement, Temperature Control and Cycling of Dialysing Fluid, Peritoneal Dialyser PD700, 1970.
Skotselanvisning for Peritoneal—Dialysapparat PD700.
Bergstrom et al., An Automated Apparatus for Peritoneal Dialysis with Volumetric Fluid Balance Measurement, reprinted from Dialysis & Transplantation, Jun./Jul. 1976.
U. Callsen, Peritoneal-Dialysator PD700, Prakt. Anasth. 9 (1974).
Piazolo et al., Erfahrungen mit einem neuen vollautomatsischen Paritoneal-dialysegerat, Munchener Medizinische Wochenschrift, 1972.
Technical Note, PD700 Peritoneal Dialyser, Jan. 29, 1979.
Assorted Photos of dialysis machine with and without casing on.
Elsevier Science Ltd., Air-Operated Diaphragm Pumps, World Pumps, Jan. 1996, at 38.
Bran & Luebbe GmbH, Diaphragm Metering Pumps, Chem. Eng'g Progress, Apr. 1987, at 18-24.
M. Schalbach, E.S. Bucherl & O. Franke, an Electronically Controlled Implantable Auxiliary Ventricle, published in Advances in Biomedical Engineering and Medical Physics: Cardiac Engineering, vol. 3.
Gene L. Mrava, Mock Circulation Systems for Artificial Hearts, published in Advances in Biomedical Engineering and Medical Physics: Cardiac Engineering, vol. 3.
W.M. Phillips, J.A. Brighton & W.S. Pierce, Artificial Heart Evaluation Using Flow Visualization Techniques, published in Transactions: American Society for Artificial Internal Organs, vol. XVIII (1972).
J.A. Brighton, W.S. Pierce, D.Landis & G. Rosenberg, Measuring Cardiac Output of Pneumatically Driven Total Artificial Hearts, published in 30th Anniversary Conference on Engineering in Medicine and Biology: Proceedings, vol. 19 (Nov. 5-9, 1977).
Operator's Instructions, Fresenius 90/2 Peritoneal Therapy Cycler (Rev. C. copyright 1991-2000).
Memorandum of Donald X. Vaccarino entitled 90/2 History File (1991-1992).
Document entitled 90/2 Cycler Software, Version 3.96 (Jan. 24, 1992).
Software Change Requests (Jul. 8, 1991-Oct. 3, 1992).
Brochure entitled Fresenius Delivers 90/2 Peritoneal Therapy Cycler (Apr. 2001).
90/2 Quick Reference.
90/2 Cycler Parts List (Nov. 6, 1997).
90/2 Cycler Box Contents.
90/2 Brochure (Jul. 1993).
90/2 Brochure (Apr. 2001).
90/2 Directions for Use.
90/2 Document Index.
Freedom Cycler Document Index.
Specification entitled Inpersol Cycler 3000 Operating Manual, List No. 21952-04, dated 1990.
Training aid entitled Learning to Use the Inpersol Cycler 3000, dated Jul. 1991.
Fresenius USA/Delmed 90/2 Peritoneal Dialysis System Operators Manual, dated Feb. 6, 1991.
Fresenius 90/2 Peritoneal Therapy Cycler Operator's Instructions, dated 2000.
Fresenius 90/2 PD Cycler Set Patient Information Card.
Fresenius Freedom Cycler Operating Instructions.
U.S. Appl. No. 11/675,492, filed Feb. 15, 2007, Alberti.
U.S. Appl. No. 11/675,495, filed Feb. 15, 2007, Bedingfield.
U.S. Appl. No. 11/675,475, filed Feb. 15, 2007, Bedingfield.
Written Opinion of the International Searching Authority for International Application No. PCT/US2008/053796 dated Jul. 29, 2008.
Defendants' Preliminary Invalidity Contentions for U.S. Patent No. 5,421,823, *Baxter Healthcare Corporation* v. *Fresenius Medical Care Holdings,* Case No. C 07-01359 PJH (JL), filed Aug. 24, 2007.

Defendants' Supplemental Invalidity Contentions for U.S. Patent No. 5,421,823, *Baxter Healthcare Corporation v. Fresenius Medical Care Holdings*, Case No. C 07-01359 PJH (JL), filed Jan. 31, 2008.

Defendants' Preliminary Invalidity Contentions for U.S. Patent No. 6,503,062, *Baxter Healthcare Corporation v. Fresenius Medical Care Holdings*, Case No. C 07-01359 PJH (JL), filed Jan. 31, 2008.

Defendants' Preliminary Invalidity Contentions for U.S. Patent No. 6,808,369, *Baxter Healthcare Corporation v. Fresenius Medical Care Holdings*, Case No. C 07-01359 PJH (JL), filed Jan. 31, 2008.

Defendants' Preliminary Invalidity Contentions for U.S. Patent No. 5,324,422, *Baxter Healthcare Corporation v. Fresenius Medical Care Holdings*, Case No. C 07-01359 PJH (JL), filed Jan. 31, 2008.

Defendants' Preliminary Invalidity Contentions for U.S. Patent No. 5,438,510, *Baxter Healthcare Corporation v. Fresenius Medical Care Holdings*, Case No. C 07-01359 PJH (JL), filed Jan. 31, 2008.

Defendants' Preliminary Invalidity Contentions for U.S. Patent No. 6,814,547, *Baxter Healthcare Corporation v. Fresenius Medical Care Holdings*, Case No. C 07-01359 PJH (JL), filed Jan. 31, 2008.

Defendants' Preliminary Invalidity Contentions for U.S. Patent No. 5,431,626, *Baxter Healthcare Corporation v. Fresenius Medical Care Holdings*, Case No. C 07-01359 PJH (JL), filed Jan. 31, 2008.

A.H. McMorris, J.L. Kelleway, B. Tapadia and E.L. Dohmann, "*Are Process Control Rooms Obsolete?*", taken from Control Engineering, pp. 42-47, Jul. 1971.

Product literature, Abbott Laboratories' LIFECARE® Blue Line System, Jul. 1990, 8 pages.

L.C. Sheppard, "*Computer Based Clinical Systems: Automation and Integration*," taken from $39^{th}$ ACEME, Sep. 13-17, 1986; pp. 73-75.

Deborah J. Mayhew, "*Principles and Guidelines in Software User Interface Designs*," Prentice-Hall, Inc., 1992, selected portions of Chapter 9 (17 pages).

Jack Shandle, "*Who Will Dominate the Desktop in the '90s? IBM and Apple Rev Their Technology Engines as the Multimedia Age Begins*," Electronics, Feb. 1990, pp. 48-50.

Product literature, Baxter Healthcare Corporation, "MultiPlex™ Series 100 Fluid Management System," copyrighted 1988, 2 pages.

Product literature, Baxter Healthcare Corporation, Flo-Gard® 6201 Volumetric Infusion Pump, copyrighted 1992, 2 pages.

Literature of I-Flow Corporation advertising its Vivus 4000™ Infusion System; presentation materials, Eric W. Brown, "*Trends in Complex I.V. Therapies for the Home Infusion Market*," presented at Advances in Drug Delivery, Dallas, Texas, Dec. 7, 1988, 10 pages.

Jerry Hirsch, "*Portable IV Frees Patients*," The Orange County Register, Nov. 21, 1991, 1 page.

Marshall D. Bedder, et al., entitled "*Cost Analysis of Two Implantable Narcotic Delivery Systems*," Journal of Pain and Symptom Management, vol. 6, No. 6, Aug. 1991, pp. 368-373.

Peter Lord, et al., "*MiniMed Technologies Programmable Implantable Infusion System*," Annals New York Academy of Sciences, pp. 66-71, describing clinical trials from Nov. 1986.

"*IEEE-488 and VXIbus Control, Data Acquisition, and Analysis . . . the Most Choices*," select pages taken from National Instruments, Application Software Products and Application Software Overview, (1991) 17 pages.

"LabVIEW® User Manual; Chapter 2, The Front Panel" taken from National Instruments Corporation, Jan. 1990; pp. 1-36.

J.C. Crone, Jaromir Belie and Roger W. Jelliffee, M.D., "*A Programmable Infusion Pump Controller*," taken from 30 Annual Conference on Engineering in Medicine and Biology, Nov. 5-9, 1977; pp. A-35826 through A-35837.

"*BLOCK Medical: Growing With Home Infusion Therapy*," taken from Invivo, The Business and Medicine Report, Apr. 1991; pp. 7-9.

James D. Foley and Andries Van Dam, "*Fundamentals of Interactive Computer Graphics*," Addison-Wesley Publishing Company, 1982, selected pages from Chapters 1 and 2 (11 pages).

Supplemental FDA 510K Notification dated Nov. 9, 1995 by Sabratek Corporation regarding Sabratek's 3030 Infusion Pump and Sabratek's Communication Link Software Package.

Response to Sabratek Corporation dated Mar. 5, 1996 to FDA request for additional information.

Bui et al, Medical Apparatus With Remote Control, US Patent Pub No. 2002/0143290 A1, Oct. 3, 2002.

Flaherty et al, Medical Apparatus Remote Control and Method, US Patent Pub No. 2002/0126036 A1, Sep. 12, 2002.

\* cited by examiner

METHOD AND APPARATUS FOR PROVIDING MEDICAL TREATMENT THERAPY BASED ON CALCULATED DEMAND

CROSS-REFERENCE TO RELATED APPLICATIONS

This application is a divisional of application Ser. No. 10/038,516 filed Jan. 3, 2002, now abandoned which is hereby incorporated by reference and upon which a claim of priority is based.

FEDERALLY SPONSORED RESEARCH OR DEVELOPMENT

None.

TECHNICAL FIELD

The present invention relates generally to a medical treatment apparatus for providing a medical treatment to a patient based on a calculated demand, and more specifically to a medical treatment administration system for delivering a medical treatment to a patient that is automatically triggered and controlled by a patient's physiological and/or environmental conditions.

BACKGROUND OF THE INVENTION

For many types of medical treatments, the impact and ultimate usefulness of the treatment depends on the patient's tolerability and sensitivity to the treatment. Such measures assist physicians in accurately and efficiently treating patients. To date, however, most medical treatments are provided to the patient based on objective measurements, rather than on actual measurements of the specific subject or environment of the subject.

For example, typical medical treatment parameters for many drug therapies are provided based on the generic circadian system. Under the circadian system it has been know in the medical industry that typical biological functions of plants and animals reoccur at approximately 24-hour intervals. In humans, the body's clock is located in the suprachiasmatic nucleus (SCN), a distinct group of cells found within the hypothalamus. The SCN controls or coordinates the circadian rhythm in the human body. Typically, a human's circadian rhythm is calibrated by the alternation of light through the eyes and darkness via melatonin secretion by the pineal gland.

Furthermore, the cellular metabolism and proliferation in normal human tissues display similar rhythms, and thus have predictable amplitudes and times of peak and trough. Such rhythms influence drug pharmacology, tolerability, and ultimate usefulness. For example, it has been thought that the circadian rhythm influences the uses and effects of anti-cancer medication, including tolerability and anti-tumor efficacy in cancer treatment. Therefore, in chronopharmacologic intervention, anti-cancer drugs are delivered according to a standard circadian rhythm, especially with chemotherapy. For example, Floxuridine delivery is typically given in four doses, each dose dependent on the time of the day:

14% of dose between 9 am and 3 pm;
68% of dose between 3 pm and 9 pm;
14% of dose between 9 pm and 3 am; and,
4% of dose between 3 am and 9 am.

Generally, the time at which the medication is delivered is selected by the physician to objectively coincide, with changes in the patient's metabolism. However, the circadian rhythm is merely an estimate of the changes in the patient's metabolism, and is not based on the actual patient's metabolism. Thus, whether the medication delivery actually coincides with the patient's actual metabolism is neither evaluated nor determined.

Additionally, different medical treatments have different optimum dosing time-profiles. For example, different anti-tumor drugs are typically dosed at different times: Epirubicin and Daunorubicin are typically dosed at 2 hours after light onset; Cyclophasphamide is typically dosed at 12 hours after light onset; Cisplatin is typically dosed at 15 hours after light onset; and, Vinblastine is typically dosed at 18 hours after light onset. As can be seen, different drugs have different mechanisms of action.

Other factors, however, may also affect proper medical treatment. For example, the minimum sensitivity of normal tissue is thought to be related to the enzyme levels that affect drug metabolism (e.g., glutathione). An overall driver of these variables is thought to be the rest-activity cycle of the patient. Because of this effect, it is known that laboratory rat studies should be conducted with the animal subjected to a 12 hour light, and 12 hour dark cycle.

Nevertheless, it is known that different patients, and with regard to cancer treatment, even different tumors, are not all on the same circadian cycle. Thus, there are at least two aspects one needs to optimize during circadian therapy: (1) the peak sensitivity of the tumor(s); and, (2) the minimum sensitivity of the normal tissues.

Standard chronopharmacologic intervention takes advantage of the circadian rhythm in drug tolerability by controlling the timing and dosing. Thus, it can reduce the effect of toxicity and improve the quality of life for the patient. Furthermore, with many drugs, including chemotherapy drugs, by administering a higher maximum tolerated dose at the least toxic circadian time, an improvement in survival may be derived. However, as explained above, there are numerous flaws with providing medical treatments following the standard circadian system.

Thus, a method and a means for subjectively determining, triggering and controlling the delivery of medical treatments for a specific patient is highly desirable.

SUMMARY OF THE INVENTION

The method and apparatus for providing medical treatment therapy of the present invention is based on actual data to calculate a strategic control. Generally, the system of the present invention comprises a medical device, a control algorithm coupled to the medical device, and a sensing device.

According to one aspect of the present invention, the sensing device automatically receives a signal and transfers the signal to the control algorithm. The control algorithm processes the signal received from the sensing device to determine whether the medical treatment should be delivered to the patient. Based on the result of the processed signal, the control algorithm develops a feedback control to control the delivery of the medical treatment to the patient.

According to another aspect of the present invention, a medical apparatus is provided for delivering a treatment to a patient. The medical apparatus comprises a medical device having a medical treatment, and a controller electrically connected to the medical device. The controller has a control algorithm stored therein that dynamically processes a signal received from a sensing device. The control algorithm develops a feedback control based on a result of processing the signal to determine whether medication should be delivered from the medical device to the patient and provides the feedback control to the medical device to control the delivery of the medical treatment to the patient.

According to another aspect of the present invention, the sensor is coupled to a patient to receive information from the patient concerning the physiological condition of the patient. The information received from the sensor is transferred to the control algorithm, where the control algorithm processes the information to control the delivery of the medication from the medical device to the patient based on the information that was processed.

According to another aspect of the present invention, the signal concerning the patient's physiological condition is selected from the group consisting of: the patient's heart rate, the patient's body temperature, the patient's activity, the patient's metabolic demand, the patient's cellular metabolism, and the patient's proliferation.

According to another aspect of the present invention, the sensor receives a signal from the patient's environment. The sensor transmits the signal to the processor, wherein the processor regulates the distribution of medical treatment from the medical device to the patient over a period of time based on a calculation of the signal.

According to another aspect of the present invention, the medical treatment administration system for delivering a medical treatment to a patient comprises a medical device and a first sensor. The medical device has a processor that regulates the distribution of medical treatment to the patient over a period of time based on a signal from the sensor. The first sensor, which is coupled to the processor, receives a signal from the patient concerning the patient's physiological condition and transmits the signal to the processor. The processor then processes the received signal to regulate the distribution of medical treatment from the medical device.

According to another aspect of the present invention, the medical treatment administration system further comprises a second sensor coupled to the processor. The second sensor obtains a signal based on a condition of the patient's environment and transmits the signal to the processor. Depending on the specific medical treatment to be administered to the patient, the processor requests the signal from one of the first sensor and second sensor.

According to another aspect of the present invention, the processor requests signals from both of the first sensor and second sensor, and the processor processes the signals and regulates the distribution of medical treatment from the medical device based on the cumulative result of the processed signals.

According to another aspect of the present invention, the sensor receives a plurality of signals from the patient concerning the patient's physiological condition and transmits the signals to the processor. The processor receives the signals, processes the signals and regulates the distribution of medical treatment from the medical device based on the cumulative result of the processed signals.

According to another aspect of the present invention, the medical treatment administration system further comprises a second medical device that delivers a medical treatment to the patient. The processor receives a signal from the second sensor, processes the second signal, and regulates the distribution of medical treatment from the second medical device to the patient.

According to another aspect of the present invention, the medical apparatus, comprises a programmable medical device for administering a medical treatment to a patient, and a controller. The programmable medical device has a first input device for entering control commands for the programmable medical device, and the controller has a second input device for entering control commands for the controller. The input devices may be located in the same location, or one or more input devices may be located at a remote location, which may or may not be the same remote location.

According to another aspect of the present invention, the sensing device of the present invention comprises a vital signs monitor coupled to the patient. The vital signs monitor obtains a first signal from the patient and transfers a second signal to the controller.

According to another aspect of the present invention, the sensing device comprises an activity sensor coupled to the patient. The activity sensor obtains a first signal from the patient and transfers a second signal to the controller.

According to another aspect of the present invention, the sensing device obtains a signal based on the cellular metabolism of the patient.

According to another aspect of the present invention, the sensing device obtains a signal based on the cellular proliferation in the patient.

According to another aspect of the present invention, the sensing device comprises a light sensor coupled to the controller, the light sensor obtaining a first signal based on the ambient light and sending a second signal to the controller.

According to another aspect of the present invention, the sensing device and the controller having the control algorithm are an integral component.

According to yet another aspect of the present invention, a method to provide medical treatment for a patient is provided. The delivery of the medical treatment may be triggered by one or more physiological or environmental conditions of the patient.

BRIEF DESCRIPTION OF THE DRAWINGS

To understand the present invention, it will now be described by way of example, with reference to the accompanying drawings in which.

DETAILED DESCRIPTION

Figure 1:
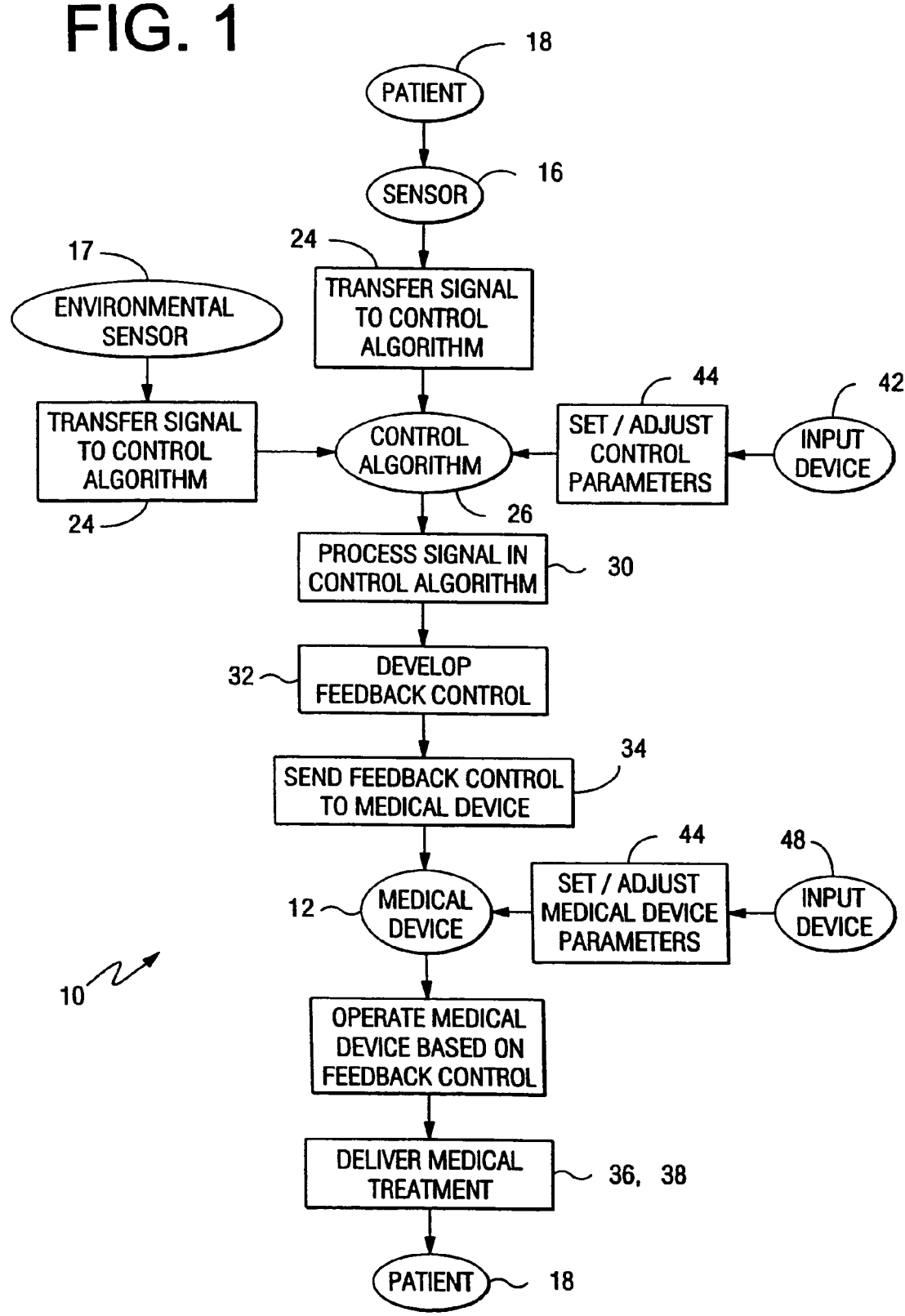
FIG. 1 is a block diagram of a medical treatment administration system of the present invention.

While this invention is susceptible of embodiments in many different forms, there is shown in the drawings and will herein be described in detail a preferred embodiment of the invention with the understanding that the present disclosure is to be considered as an exemplification of the principles of the invention and is not intended to limit the broad aspect of the invention to the embodiment illustrated.

Referring now in detail to the Figures, there is shown a medical treatment administration system 10 utilizing a medical treatment delivery control to distribute the medical treatment based on the condition of the specific patient and/or a change in the environment of the specific patient. As shown in FIG. 1, one embodiment of the medical treatment administration system 10 includes a medical device 12, a control algorithm 26 coupled to the medical device 12, and a sensor 16 coupled to the patient 18. The medical device 12 may be one of a variety of devices, including, but not limited to infusion pumps, ventilators, insulin delivery devices, and anesthesia delivery devices, however, one of ordinary skill in the art would understand that other medical devices could be utilized without departing from the scope of the invention. Additionally, the medical device 12 may be a programmable medical device.

Figure 9:
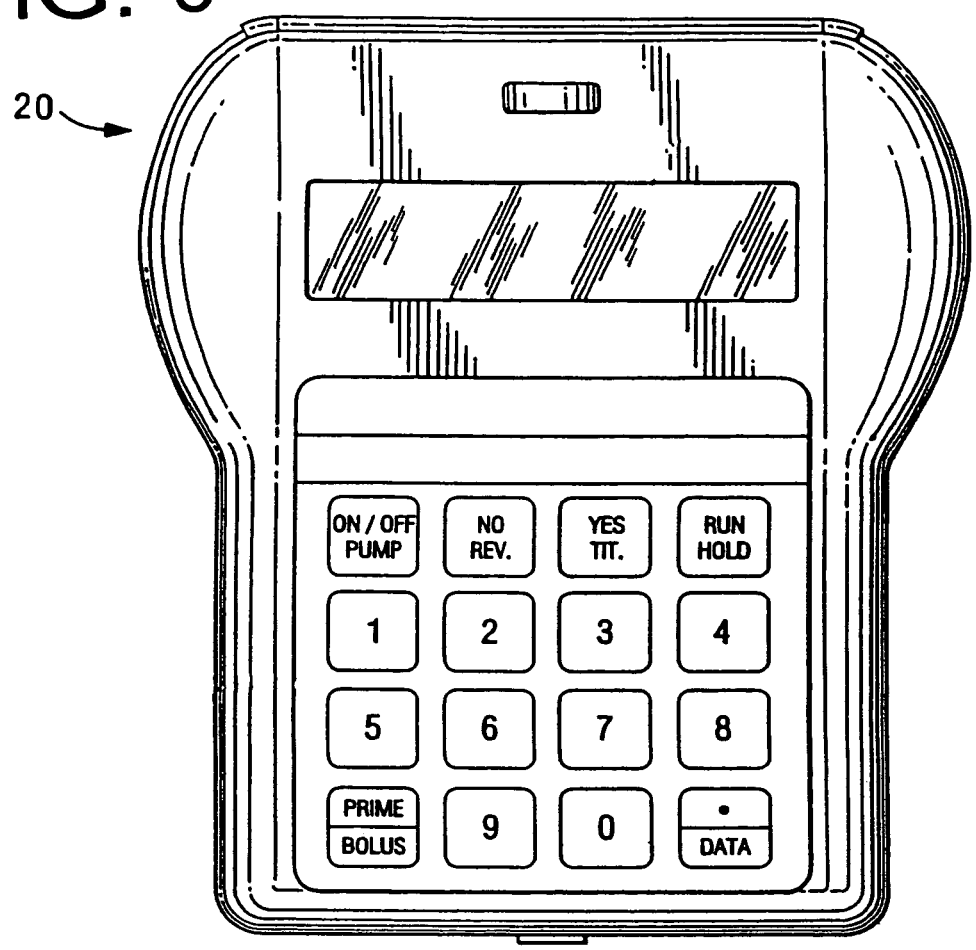
FIG. 9 is a front elevation view of one embodiment of an infusion pump utilized with the present invention.

In one embodiment, an infusion pump 20, illustrated in FIG. 9, is utilized as the medical device 12 for administering a liquid medicant to the patient 18. Typically, the medical device 12 has a supply of medication (not shown) and a means for delivering the medication (not shown) to the patient 18. With the infusion pump 20, the supply of medication is typically a liquid medicant retained in a syringe or IV-type bag. Additionally, with an infusion pump 20 the means for delivering the medication includes a liquid injection device, often a hollow needle or catheter, adapted to be connected to the patient, a conduit or tubing connected to the liquid injection device, a pumping mechanism for pumping the liquid medicant through the conduit and into the patient via the liquid injection device, and a controller for controlling the pumping mechanism. However, when other types of medical devices are utilized, the medical treatment and the means for delivering the treatment will likely vary to be in accord with the specific medical device. For example, a ventilator provides oxygen to the patient, an insulin delivery mechanism delivers insulin to the patient, and an anesthesia device provides anesthesia gas or anesthesia medication to the patient.

In the embodiment illustrated in FIG. 1, the sensor 16 is coupled to the patient 18 and receives information from the patient 18 concerning the physiological condition of the patient 18. As is understood by one of ordinary skill in the art, such physiological conditions may include, but are not limited to, the patient's heart rate, the patient's body temperature, the patient's blood pressure, the patient's activity level, the patient's cellular metabolism, the patient's cellular proliferation, the patient's metabolic demand, the patient's $SpO_2$ level, etc. Such factors, as well as other factors known by one of ordinary skill in the art, are understood to be triggering events for the distribution of medical treatment, and especially drug therapy, to individuals in the treatment of medical conditions. Additionally, the sensing device may comprise an input device for receiving a manual input. The manual input may be provided by a health care provider or the patient. One example of the patient providing input for the sensing device is where the medical device 12 is a insulin delivery mechanism. As such, the patient may provide input to the sensor indicating the type of food consumed by the patient.

In one embodiment, multiple sensors 16 are comprised in a portable multiparametric physiological monitor for continuous monitoring of certain physical parameters of the patient. The monitor has sensors 16 including: EKG electrodes, a chest expansion sensor, an accelerometer, a chest microphone, a barometric pressure sensor, a body temperature sensor and an ambient temperature sensor. Each of the sensors provides an output signal to an analog-to-digital converter (ADC).

In such an embodiment, the sensors 16 may be provided in a body strap (not shown) which, could comprise a chest strap upon which are distributed the various sensors and supporting electronics. (It will be recognized by those skilled in the art that a multiparametric monitoring device may also be mounted by a strap about a part of the body other than the chest). The chest strap is adapted to fit around the torso of the patient 18.

The variety of parametric sensors 16 are located on the strap as most appropriate for the parameter (or parameters) which it detects. Each of the sensors 16 provides an electrical input to analog circuitry which filters and amplifies the sensor signals, as known in the art of signal processing, and outputs them to an analog-to-digital converter, which may be part of controller hardware. The sensors in the strap may be as follows: a pectoralis temperature sensor which senses the temperature of the surface of the patient's chest; barometric pressure sensor which senses the ambient barometric pressure of the patient's environment; chest expansion (ventilation) sensor which detects the tension on the chest strap as an indication of the expansion and contraction of the patient's chest; accelerometer which detects movement and inclination of the patient's body; ambient temperature sensor which senses the ambient temperature of the patient's environment; microphone which detects sounds from within the patient's torso; underarm temperature sensor which senses the temperature of the side of the patient's torso underneath the arm; and, EKG electrodes which detect electrical signals caused by action of the heart muscle. The EKG electrodes are used in combination with ground, or reference, electrodes, and are placed in contact with the skin of the patient's chest to detect electrical signals generated by the pumping action of the patient's heart muscle. The EKG (electrocardiogram) is an indication of the patient's heart activity, as is well known in the field of medicine.

Also as shown in FIG. 1, sensor 17 may be provided in addition to, or in substitution of, sensor 16. Sensor 17 obtains information concerning the environment of the patient 18. Typically, the sensors 16,17 automatically obtain the signal concerning the physiological condition of the patient and/or the condition of the environment, respectively, without intervention from the patient 18. Depending on the information required by the control algorithm 26, multiple sensors 16,17 may be utilized in series or in parallel (FIGS. 1, 4, 7 and 8).

Figure 4:
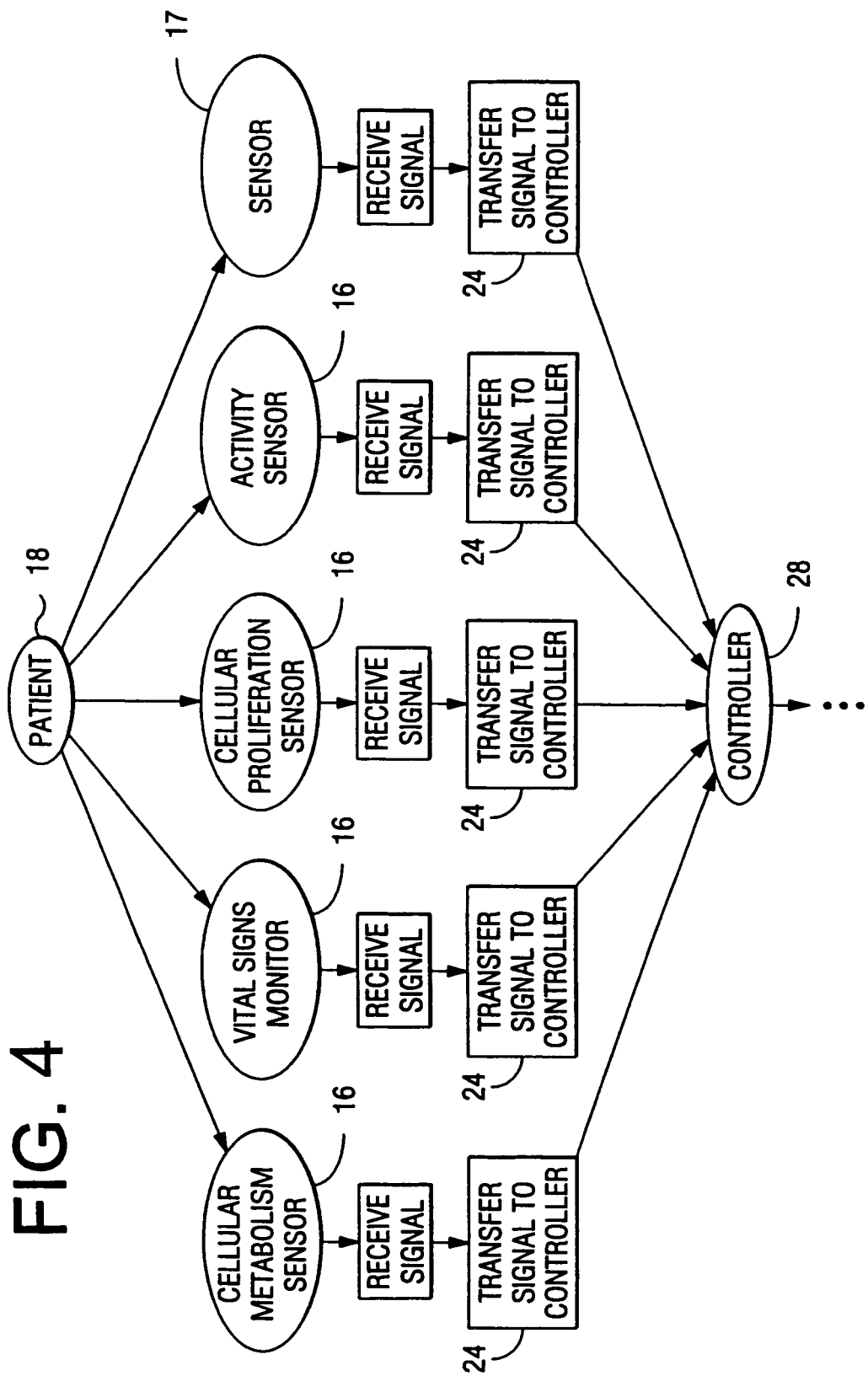
FIG. 4 is a block diagram of another variation of the medical treatment administration system of FIG. 1, including a variety of sensing devices.
Figure 5:
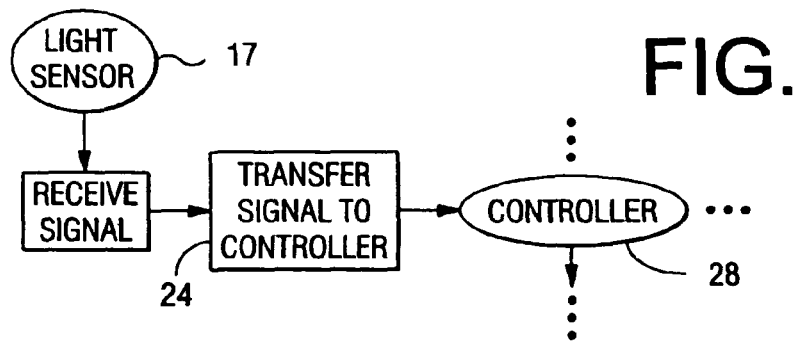
FIG. 5 is a block diagram of another variation of the medical treatment administration system of FIG. 1, including a variety of sensing devices.
Figure 6:
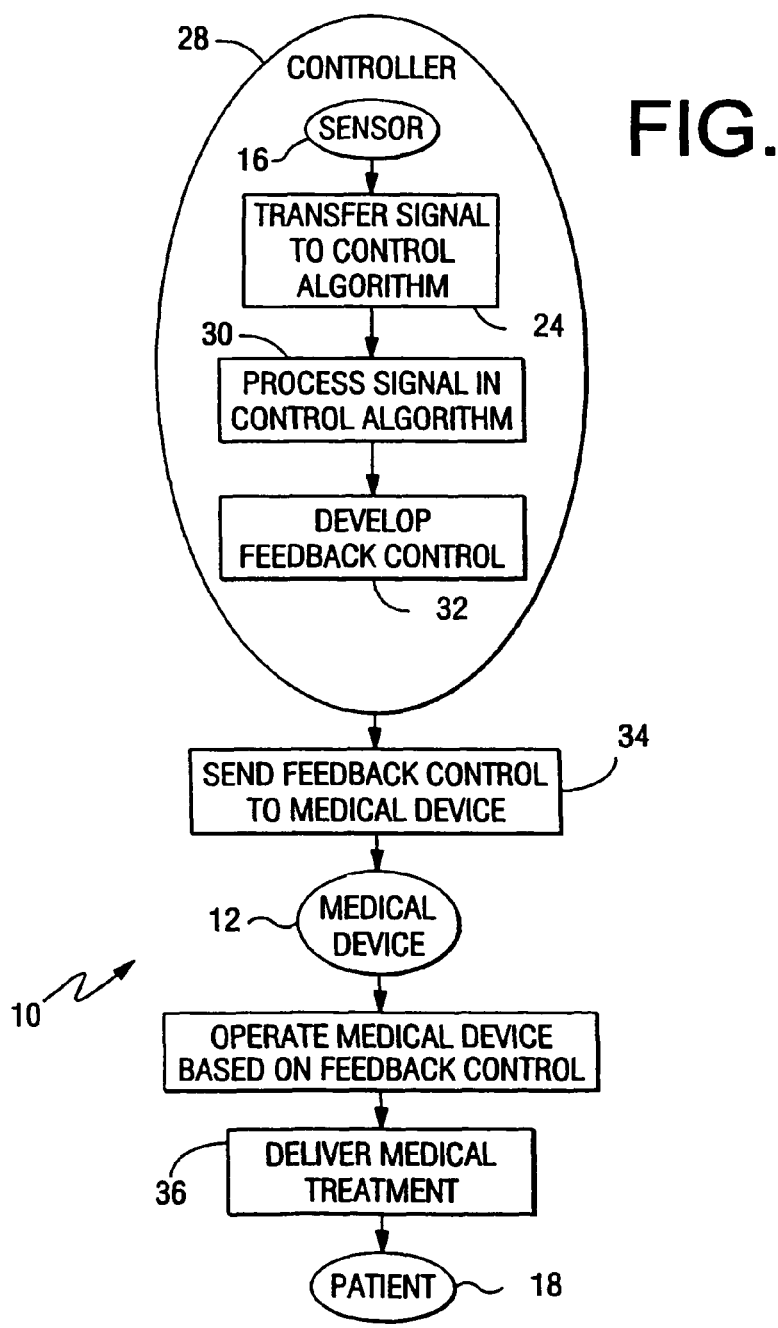
FIG. 6 is a block diagram of another variation of the medical treatment administration system of FIG. 1, including where the controller and the sensing device are an integral component.

The sensors 16,17 may be any device that is capable of receiving a signal (i.e., information), whether from an individual 16, such as a signal concerning the individuals heart rate, body temperature, blood pressure, activity level, cellular metabolism, cellular proliferation, metabolic demand, $SpO_2$ level, etc., or based on an environmental condition 17, such as the ambient temperature, ambient light condition, etc. As shown in FIGS. 4 and 5, such sensors 16,17 may include, but are not limited to, vital signs monitors, blood pressure monitors, light sensors, environmental sensors and activity sensors. Additionally, as shown in FIG. 6, rather than being a separate component, the sensors 16,17 may be integral with the controller 28.

Figure 2:
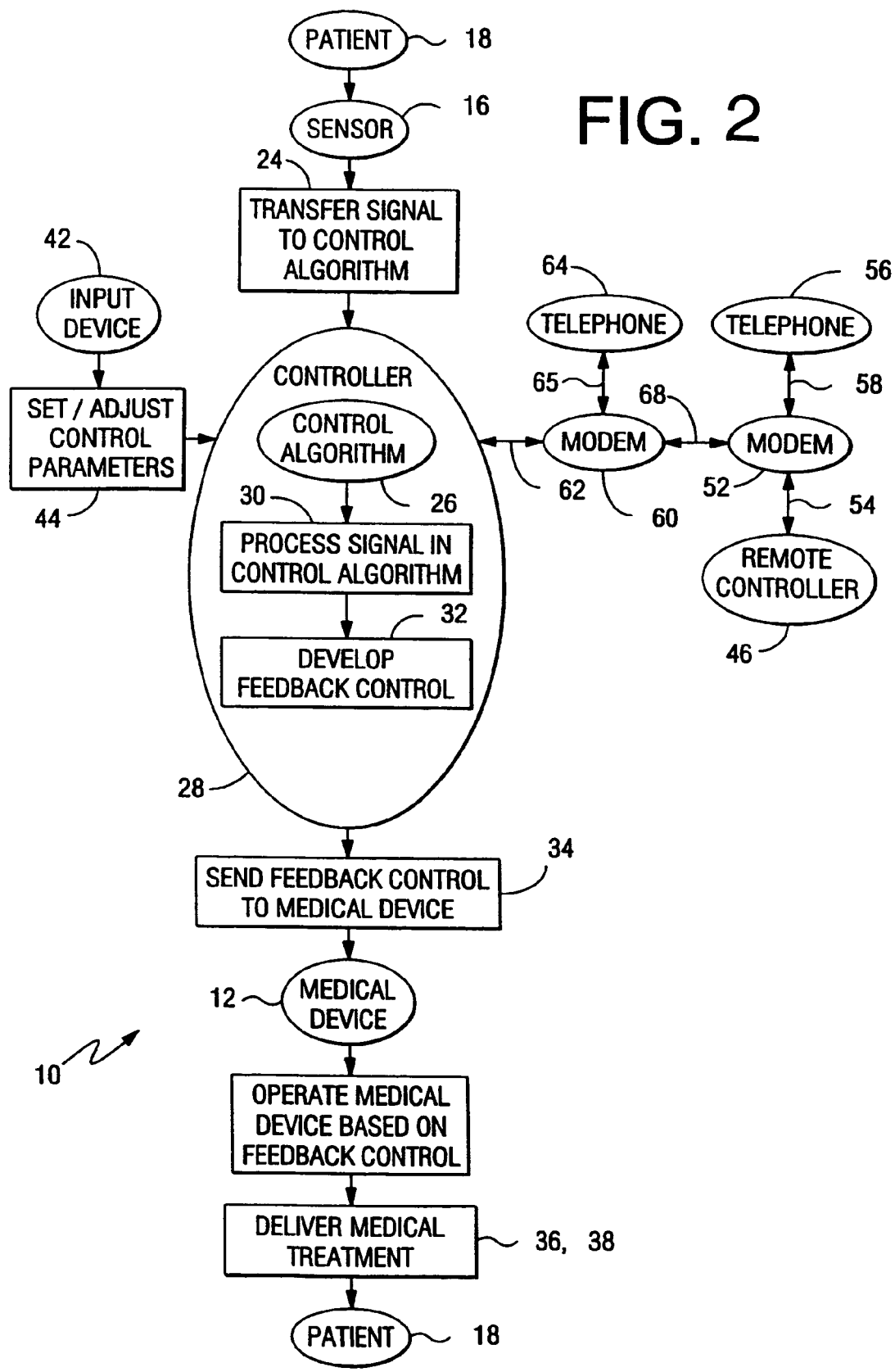
FIG. 2 is a block diagram of a variation of the medical treatment administration system of FIG. 1, including remote controlling.
Figure 3:
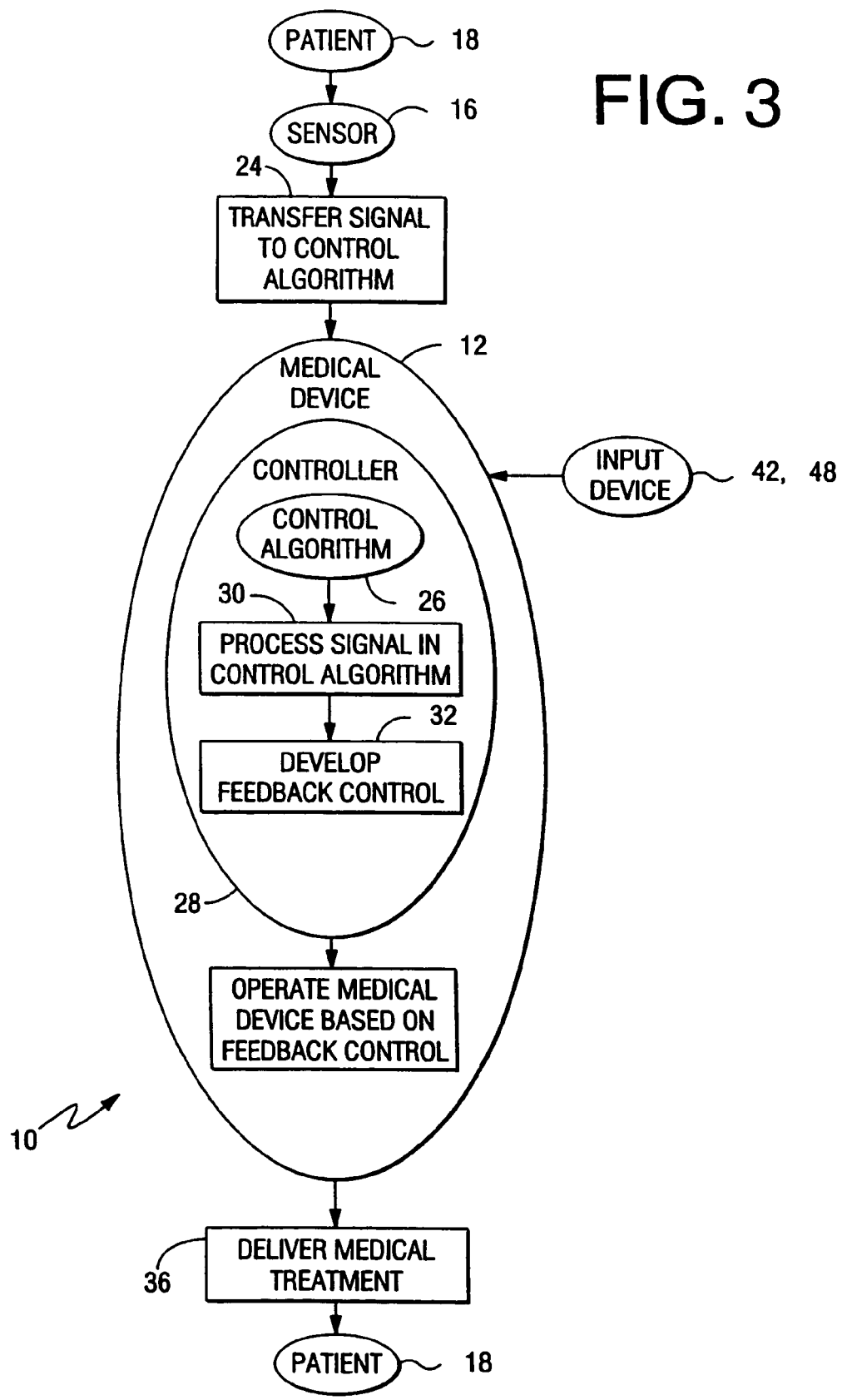
FIG. 3 is a block diagram of another variation of the medical treatment administration system of FIG. 1, including where the controller is a component of the medical device.

The signal received from the sensor 16,17 is electrically transferred 24 to a control algorithm 26. As shown in FIGS. 2, 3 and 6, the control algorithm 26 may be a part of the controller 28 (also referred to as a processor). Additionally, as shown in FIG. 3, the controller 28 may be a component of the medical device 12. Depending on the specific medical treatment to be administered to the patient 18, the control algorithm 26 may request signals from one or more sensors 16,17. While it is understood that the rest-activity or metabolism cycle of a patient can be determined invasively by measuring various elements including blood cell counts, plasma or serum concentration of cortisol, liver enzymes, and creatine, other methods may also be available. For example, the rest-activity or metabolism cycle of a patient can also be measured non-invasively by the vital sign or activity of the patient. Additionally, it has been found that the body temperature of a patient drops during the night, and that a patient's heart rate drops when the patient is at rest. Accordingly, such signals are obtained by the sensors 16,17, and such information is transferred 24 to the control algorithm 26 for processing.

Figure 10:
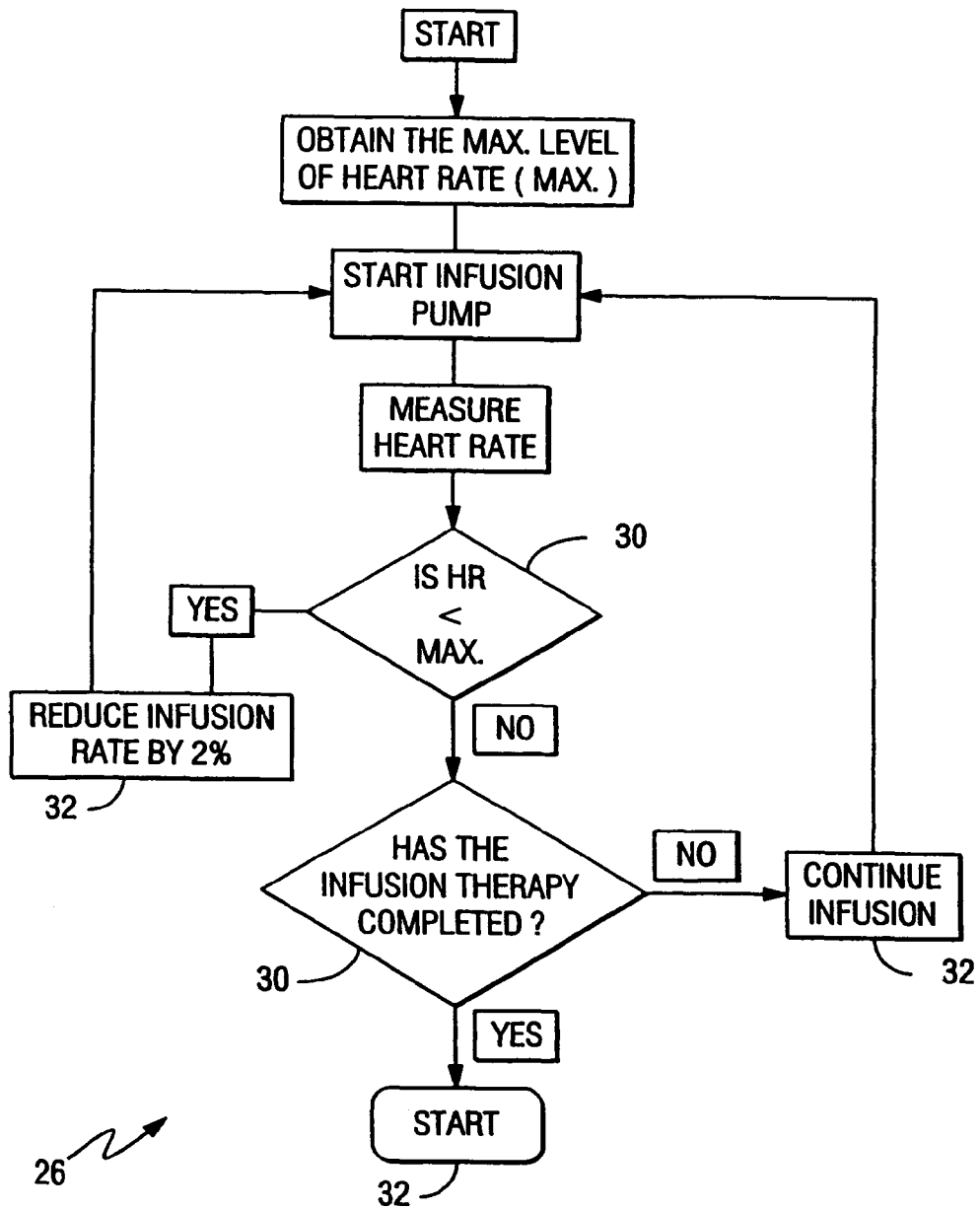
FIG. 10 is a block diagram of one type of a control algorithm of the present invention.

It is understood that the control algorithm 26 will likely be different for each different medical treatment, and further it is also understood that the control algorithm 26 may be different for different patients, even for the same medical treatment. One example of a control algorithm 26 is shown in FIG. 10. As shown in FIG. 10, the control algorithm 26 is utilized to control the delivery of medication to a patient as a function of the patient's 18 heart rate. In this embodiment the control algorithm 26 receives a signal of the patient's heart rate from one of the sensors 16. The control algorithm 26 continually processes the signal 30 by comparing the signal with the maximum heart rate. If the heart rate signal is less than the maximum heart rate signal the control algorithm develops a feed back control 32 to reduce the rate of infusion of the infusion pump 12 by 2%. If the heart rate signal is not less than the maximum heart rate signal the control algorithm further determines if the infusion therapy has been completed. If the infusion therapy has not been completed, feedback control 32 is provided to continue infusion. Additional processing 30 of the heart rate signal is subsequently continued. If the infusion therapy has been completed, feedback control 32 is provided to stop the infusion pump 12.

After the control algorithm 26 receives the transferred signal 24 it processes 30 the signal through the control algorithm 26 and a resultant feedback control 32 is developed. If multiple signals are requested and received from a plurality of sensors 16,17, and are required in order to determine if the medical treatment is to be delivered to the patient 18, each required signal is processes 30 through the control algorithm 26 as programmed, and a resultant feedback control 32 is developed. The feedback control 32 operates as a control signal for the medical device 12 to control or regulate delivery of the medical treatment to the patient 18.

This is accomplished by transferring 34 the feedback control 32 that was developed by the control algorithm 26 to the medical device 12. The feedback control 32 provides the commands for operation of the medical device 12. As shown in FIG. 1, the feedback control 32 typically provides one of two signals or commands to the medical device 12: deliver 36 medical treatment to the patient 18 or do not deliver 38 medical treatment to the patient. If the feedback control 32 provides a signal to deliver 36 the medical treatment it may also provide a signal to the medical device 12 indicating the amount and rate of treatment to provide to the patient 18.

Figure 7:
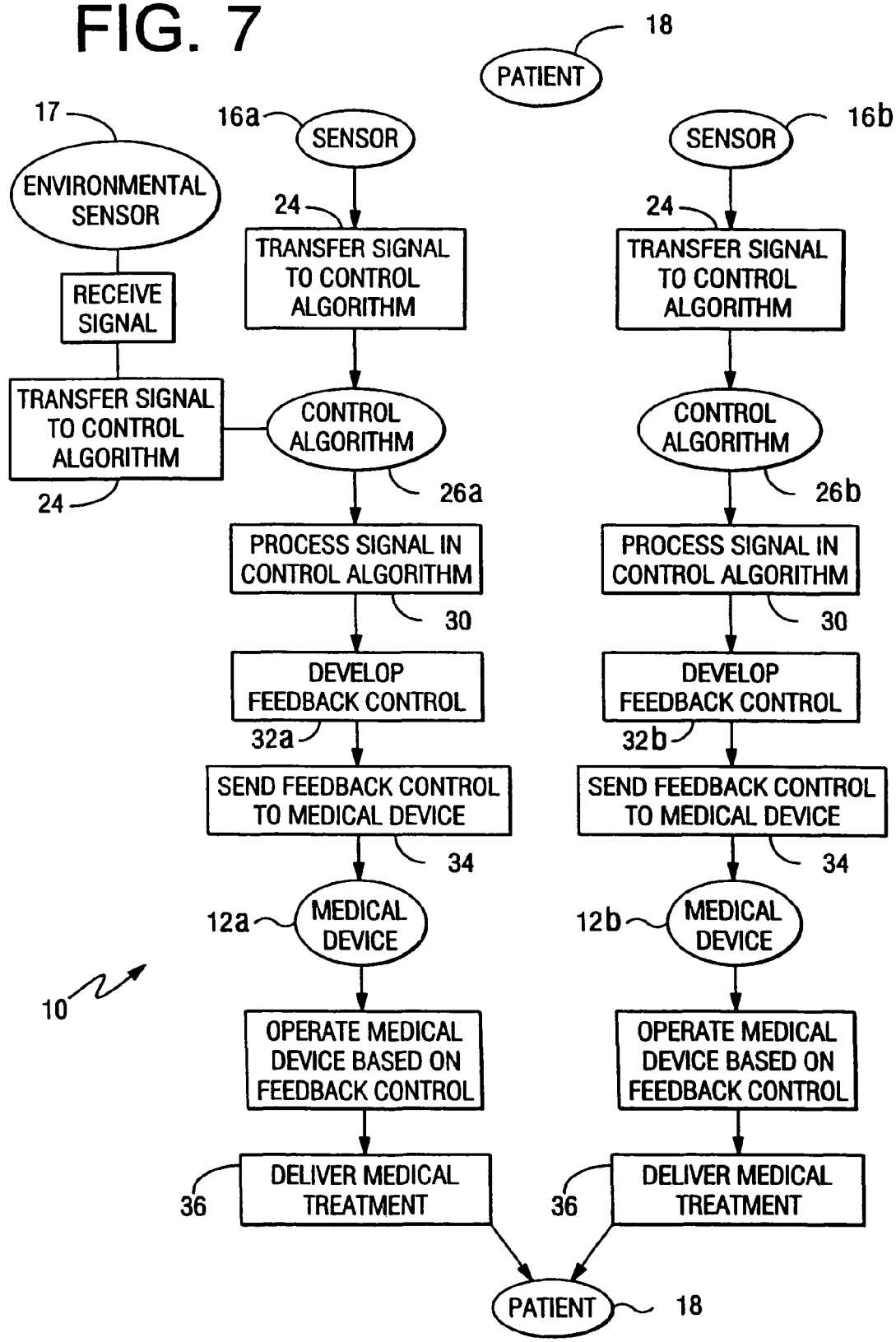
FIG. 7 is a block diagram of another variation of the medical treatment administration system of FIG. 1, including a plurality of medical treatment devices.

As shown in FIG. 7, multiple medical devices 12a, 12b may be utilized to deliver 36 medical treatments to the patient 18. The specific medical treatments may be the same, and may merely be dosed differently, or each medical device 12a,12b may deliver 36 a different medical treatment to the patient 18. Further, as also shown in FIG. 7, separate control algorithms 26a,26b may be utilized for each medical device 12a,12b, respectively. The embodiment of FIG. 7, utilizes two distinct control algorithms 26a,26b, and numerous sensors 16a, 16b and 17. Sensors 16a, 17 transfer 24 signals to control algorithm 26a, which, depending on the treatment to be delivered 36 to the patient 18, may process 30 the signals from one or both of the sensors 16a,17 to develop a resultant feedback control 32a. Sensor 16b transfers 24 a signal to control algorithm 26b which likewise processes 30 the signal and develops a resultant feedback control 32b. Feedback control 32a is sent to the first medical device 12a to control the delivery 36a of medical treatment to the patient 18, while feedback control 32b is sent to the second medical device 12b to control the delivery 36b of medical treatment to the same patient 18.

Figure 8:
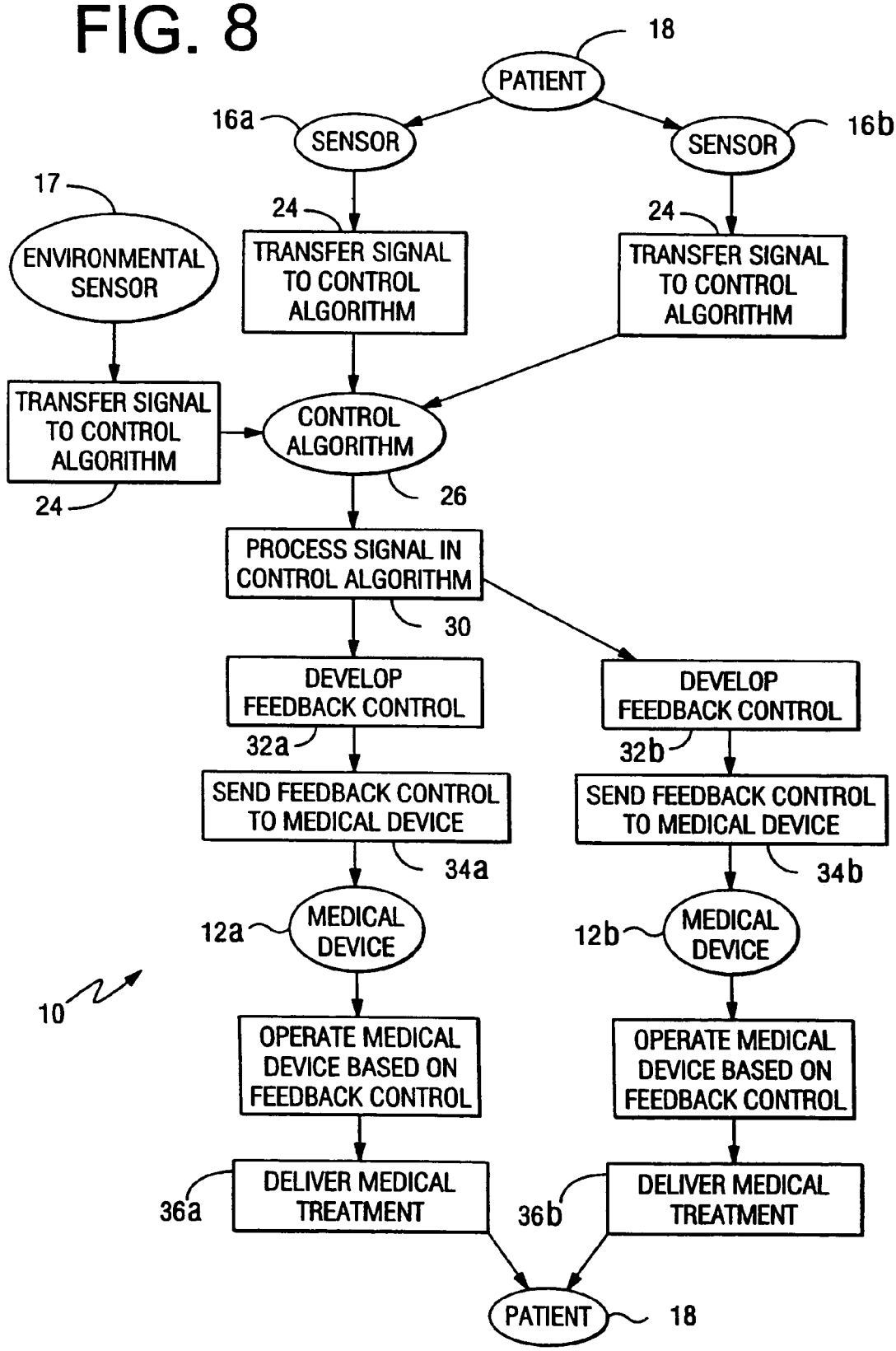
FIG. 8 is a block diagram of another variation of the medical treatment administration system of FIG. 7, including a processor for a plurality of medical treatment devices.

Conversely, as shown in FIG. 8, one control algorithm 26 may control multiple medical devices 12a,12b. In this embodiment, one control algorithm 26 is utilized with a plurality of sensors 16a, 16b and 17. Sensors 16a, 16b and 17 transfer 24 signals to the control algorithm 26, which, depending on the treatment to be delivered 36 to the patient 18, may process 30 the signals from one or more of the sensors 16a, 16b and 17 to develop one or more resultant feedback controls 32a,32b. Feedback control 32a is sent to the first medical device 12a to control the delivery 36a of medical treatment to the patient 18, while feedback control 32b is sent to the second medical device 12b to control the delivery 36b of medical treatment to the same patient 18. Accordingly, in this embodiment the control algorithm 26 for the first medical device 12a is the same control algorithm 26 as for the second medical device 12b.

Because the medical treatment apparatus 10 may be utilized with different treatment therapies, the control algorithm 26 is generally modified or changed for each different treatment therapy. Thus, as shown in FIGS. 1 and 2, an input device 42 is generally provided to adjust and set the control parameters 44 of the control algorithm 26. The input device 42 may be coupled to the controller 28 or directly to the control algorithm 26. While the control algorithm 26 may be manually input, it may also be dynamically downloaded as from a database or network.

Further, as shown in FIG. 1, the medical device 12 may also have an input device 48 therefor. The input device 48 for the medical device 12 allows a user, typically an authorized clinician to enter control commands 50 to adjust or set control parameters for the medical device 12. In an alternate embodiment, the input device for the medical device 12 is the same as the input device for the controller/control algorithm.

As shown in FIG. 2, a remote controller 46 (i.e., a remote input device) may be provided for remotely adjusting or setting the control parameters of the control algorithm 26 and/or controller 28. The remote controller 46 is disposed at a room location (i.e. a second location) remote from the room location at which the medical device 12 is located (i.e., a first location). The remote controller 46 could be disposed in a different room of the same building in which the medical device 12 is disposed, or in a different building than the one in which the medical device 12 is disposed. The remote controller 46 is connected to a conventional voice/data modem 52 via a data link 54, and the modem 52 is also connected to a telephone 56 via a voice link 58. The medical device 12 is connected to a conventional voice/data modem 60 via a data link 62, and the modem 60 is connected to a telephone 64 via a voice link 66. The two modems 52, 60 are interconnected to bidirectional voice and data communication via a communication link 68, which could be a telephone line, for example. Additionally, the remote controller 46 may communicate with the control algorithm 26 via an internet, an intranet and a wireless network. Furthermore, the remote controller 26 may be a server.

While the specific embodiments have been illustrated and described, numerous modifications come to mind without significantly departing from the spirit of the invention, and the scope of protection is only limited by the scope of the accompanying Claims.

What is claimed is:

1. A medical treatment apparatus for providing medication to a patient, comprising:
    a medical fluid pump;
    a controller in communication with the pump and having a control algorithm stored thereon;
    a sensor for coupling to a patient to receive information from the patient concerning the physiological condition of the patient, the information being transferred from the sensor to the control algorithm; and
    a light sensor that receives information about an ambient light environment from an environment of the patient, the information about the ambient light environment being transferred to the control algorithm,
    wherein the control algorithm is adapted to process the information from both the sensor coupled to the patient and the sensor that receives the information about the ambient light environment to determine a circadian rhythm specific to the patient and control an amount and rate of the delivery of the medication to the patient based on the determined circadian rhythm of the patient by transmitting a command to the pump.

2. The medical treatment apparatus of claim 1, further comprising an input device for adjusting parameters of the control algorithm.

3. A medical apparatus for delivering a treatment to a patient, comprising:
    a medical fluid pump for pumping a medical fluid to provide a medical treatment; and
    a controller electrically connected to the medical fluid pump, the controller:
    dynamically processing a first signal received from a first sensing device connected to the patient, and a second signal from a second sensing device, the second signal relating to information as to a temperature and light environment of the patient,
    developing a feedback control based on a result of processing both the first and second signals to determine a circadian rhythm specific to the patient, and
    controlling an amount and rate of the delivery of the medical treatment to the patient based on the determined circadian rhythm of the patient by transmitting a command to the pump.

4. The medical apparatus of claim 3, further comprising a control algorithm electronically connected to the controller, wherein the control algorithm processes the signals received from the sensing devices, and wherein the control algorithm develops a feedback control based on the result of processing the signals for the delivery of medication to the patient.

5. The medical apparatus of claim 4, wherein the control algorithm for the controller is downloaded to the controller.

6. The medical apparatus of claim 3, wherein the medical fluid pump pumps from a supply of medication.

7. The medical apparatus of claim 3, wherein the first signal is automatically obtained from a physiological condition of the patient without intervention from the patient.

8. The medical apparatus of claim 3, wherein the second signal is automatically obtained from the second sensing device without intervention from the patient.

9. The medical apparatus of claim 3, wherein the controller is housed with the pump.

10. The medical apparatus of claim 3, further comprising an input device coupled to the controller, the input device provided to allow an authorized user to manipulate the control algorithm.

11. The medical apparatus of claim 10, wherein the input device is a remote controller located at a second location distinct from a first location, and wherein the medical fluid pump is located at the first location.

12. The medical apparatus of claim 3, wherein the first sensing device comprises a vital signs monitor coupled to the patient, the vital signs monitor obtaining a signal from the patient.

13. The medical apparatus of claim 3, wherein the first sensing device comprises an activity sensor coupled to the patient, the activity sensor obtaining a signal from the patient.

14. The medical apparatus of claim 3, wherein the second sensing device comprises a light sensor coupled to the controller, the light sensor obtaining a signal based on the ambient light.

15. The medical apparatus of claim 3, wherein the second sensing device comprises an environmental sensor coupled to the controller, the environmental sensor obtaining a first signal based on an environmental factor of the environment of the patient and sending a second signal to the controller.

16. A medical treatment administration system for delivering a medical treatment to a patient, comprising:
    a medical device for delivering a medical treatment to a patient, the medical device having a processor to regulate the distribution of medical treatment to the patient over a period of time;
    a first sensor coupled to the processor, the first sensor receiving a signal from the patient concerning the patient's physiological condition and transmitting the signal to the processor; and,
    a second sensor coupled to the processor and receiving a signal from an environment of the patient and transmitting the signal to the processor, the processor:
    receiving the signals from the first and second sensors,
    processing the signals to determine a circadian rhythm of the patient, and
    regulating an amount and rate of the distribution of medical treatment from the medical device based on the circadian rhythm of the patient by transmitting a command to the medical device.

17. The medical treatment administration system of claim 16, wherein the first sensor is an input device that receives manual input.

18. The medical treatment administration system of claim 16, wherein the processor has a control algorithm that processes the signal from at least one of the first and second sensors.

19. The medical treatment administration system of claim 16, wherein based on the specific medical treatment to be administered to the patient, the processor processes the signal from one of the first sensor and second sensor.

20. The medical treatment administration system of claim 16, wherein based on the specific medical treatment to be administered to the patient, the processor processes signals from both of the first sensor and second sensor, and wherein the processor regulates the distribution of medical treatment from the medical device based on the cumulative result of the processed signals.

* * * * *

UNITED STATES PATENT AND TRADEMARK OFFICE
CERTIFICATE OF CORRECTION

Page 1 of 1

PATENT NO. : 8,545,435 B2
APPLICATION NO. : 11/078805
DATED : October 1, 2013
INVENTOR(S) : Tuan Bui It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1257 days.

Signed and Sealed this
Seventh Day of April, 2015

Michelle K. Lee
*Director of the United States Patent and Trademark Office*